United States Patent
Yamamoto et al.

(10) Patent No.: US 12,227,542 B2
(45) Date of Patent: Feb. 18, 2025

(54) METHOD FOR PRODUCING PEPTIDE COMPOUND, PROTECTIVE GROUP-FORMING REAGENT, AND CONDENSED POLYCYCLIC COMPOUND

(71) Applicant: FUJIFILM CORPORATION, Tokyo (JP)

(72) Inventors: Yosuke Yamamoto, Kanagawa (JP); Makoto Takahashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/558,542

(22) Filed: Dec. 21, 2021

(65) Prior Publication Data

US 2022/0112234 A1    Apr. 14, 2022

Related U.S. Application Data

(63) Continuation of application No. PCT/JP2020/024232, filed on Jun. 19, 2020.

(30) Foreign Application Priority Data

Jun. 28, 2019  (JP) .................................. 2019-122492
Dec. 6, 2019   (JP) .................................. 2019-221545

(51) Int. Cl.
    C07K 1/06       (2006.01)
(52) U.S. Cl.
    CPC .................................. C07K 1/065 (2013.01)
(58) Field of Classification Search
    None
    See application file for complete search history.

(56) References Cited

U.S. PATENT DOCUMENTS

| | | | |
|---|---|---|---|
| 5,306,562 A | 4/1994 | Barany | |
| 2009/0299103 A1 | 12/2009 | Chiba et al. | |
| 2010/0029904 A1 | 2/2010 | Chiba et al. | |
| 2010/0240867 A1 | 9/2010 | Takahashi | |
| 2010/0249374 A1 | 9/2010 | Takahashi | |
| 2011/0160433 A1 | 6/2011 | Takahashi | |
| 2012/0059149 A1 | 3/2012 | Takahashi | |
| 2014/0046022 A1 | 2/2014 | Takahashi | |
| 2014/0213761 A1 | 7/2014 | Takahashi | |
| 2016/0060198 A1 | 3/2016 | Takahashi | |
| 2019/0023726 A1 | 1/2019 | Yano et al. | |
| 2019/0263842 A1 | 8/2019 | Yano et al. | |
| 2020/0325163 A1 | 10/2020 | Yano et al. | |
| 2021/0079028 A1 | 3/2021 | Yano et al. | |
| 2021/0380633 A1 | 12/2021 | Yamamoto et al. | |
| 2021/0380634 A1 | 12/2021 | Yamamoto et al. | |

FOREIGN PATENT DOCUMENTS

| | | | |
|---|---|---|---|
| EP | 3489245 A1 | 5/2019 | |
| JP | 2000-044493 A | 2/2000 | |
| JP | 2009-185063 A | 8/2009 | |
| WO | 2007/034812 A1 | 3/2007 | |
| WO | 2010/104169 A1 | 9/2010 | |
| WO | 2010/113939 A1 | 10/2010 | |
| WO | 2011/078295 A1 | 6/2011 | |
| WO | 2017/038650 A1 | 3/2017 | |
| WO | 2018/021233 A1 | 2/2018 | |
| WO | 2019/123994 A1 | 6/2019 | |
| WO | 2019184089 A1 | 10/2019 | |
| WO | 2020/175472 A1 | 9/2020 | |
| WO | 2020/175473 A1 | 9/2020 | |

OTHER PUBLICATIONS

English language translation of the following: Office action dated Nov. 29, 2022 from the JPO in a Japanese patent application No. 2021-526942 corresponding to the instant patent application. This office action translation is submitted now in order to supplement the understanding of the cited reference which is being disclosed in the instant Information Disclosure Statement.

Extended European Search Report dated Jun. 23, 2022, issued in corresponding EP Patent Application No. 20831684.4.

Brega, V. et al., "Polymer Amphiphiles for Photoregulated Anticancer Drug Delivery", ACS Applied Materials and Interfaces, 2019, vol. 11, pp. 2814-2820, Dec. 24, 2018.

International Search Report issued in International Application No. PCT/JP2020/024232 on Sep. 8, 2020.

Written Opinion of the ISA issued in International Application No. PCT/JP2020/024232 on Sep. 8, 2020.

(Continued)

*Primary Examiner* — Thomas S Heard

(74) *Attorney, Agent, or Firm* — SOLARIS Intellectual Property Group, PLLC

(57) ABSTRACT

Provided are a method for producing a peptide compound including a step of using a compound represented by Formula (1); a protective group-forming reagent including the compound; and the compound. At least one of $R^1$ to $R^8$ or $Y^2$ has $R^A$, $R^A$ represents an aliphatic hydrocarbon group or an organic group having an aliphatic hydrocarbon group, and the number of carbon atoms in at least one aliphatic hydrocarbon group is 12 or more. However, $R^A$ does not have a silyl group and a hydrocarbon group having a silyloxy structure.

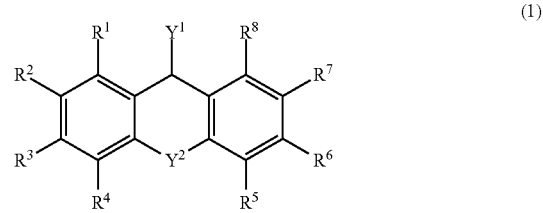

(1)

7 Claims, No Drawings

(56) References Cited

OTHER PUBLICATIONS

Written Opinion of the IPEA issued in International Application No. PCT/JP2020/024232 on Mar. 30, 2021.
International Preliminary Report on Patentability issued in International Application No. PCT/JP2020/024232 on Aug. 17, 2021.
Kaucher, M. S. et al., "Selective Transport of Water Mediated by Porous Dendritic Dipeptides", Journal of the American Chemical Society, 2007, vol. 129, No. 38, pp. 11698-11699.
Registry (STN) [ online ], Jan. 27, 1993 [ retrieval date: May 7, 2020 ] CAS: 145543-42-6 entire text, structural formulas.
Registry ( STN ) [ online ], Jan. 27, 1993 [ retrieval date : May 7, 2020 ] CAS: 145543-43-7 entire text, structural formulas.
Registry ( STN ) [online], Sep. 18, 2013 [Retrieval date: May 7, 2020] CAS: 1452164-35-0 entire text, structural formulas.
Torikai, K. et al., "N (π)-2-Naphthylmethoxymethyl-Protected Histidines: Scalable, Racemization-Free Building Blocks for Peptide Synthesis", Organic Process Research & Development, Feb. 19, 2020 vol. 24, No. 3, p. 448-453.
International Search Report issued in International Application No. PCT/JP2020/007477 on Jun. 2, 2020.
Written Opinion of the ISA issued in International Application No. PCT/JP2020/007477 on Jun. 2, 2020.
International Search Report issued in International Application No. PCT/JP2020/007478 on Jun. 2, 2020.
Written Opinion of the ISA issued in International Application No. PCT/JP2020/007478 on Jun. 2, 2020.
Office action dated Feb. 11, 2022 from the IPO in a Indian patent application No. 202147060531 corresponding to the instant patent application.
English language translation of the following: Office action dated Nov. 21, 2023 from the TIPO in a Taiwan patent application No. 109121463 corresponding to the instant patent application. This office action translation is submitted now in order to supplement the understanding of the cited reference which is being disclosed in the instant Information Disclosure Statement.

METHOD FOR PRODUCING PEPTIDE COMPOUND, PROTECTIVE GROUP-FORMING REAGENT, AND CONDENSED POLYCYCLIC COMPOUND

CROSS-REFERENCE TO RELATED APPLICATIONS

This application is a Continuation of International Application No. PCT/JP2020/024232 filed on Jun. 19, 2020, which claims priority to Japanese Patent Application No. 2019-122492 filed on Jun. 28, 2019 and Japanese Patent Application No. 2019-221545 filed on Dec. 6, 2019. The entire contents of these applications are incorporated herein by reference.

BACKGROUND OF THE INVENTION

1. Field of the Invention

The present disclosure relates to a method for producing a peptide compound, a protective group-forming reagent, and a condensed polycyclic compound.

2. Description of the Related Art

Examples of a method for producing peptide include a solid phase method and a liquid phase method.

The solid phase method is advantageous in that an isolation and purification after a reaction can be performed only by washing the resin. However, the solid phase method is associated with problems in that the reaction is essentially a heterogeneous phase reaction, a reaction reagent need to be used in excess to compensate for the low reactivity, and tracing of the reaction and analysis of a reaction product supported by a carrier are difficult.

On the other hand, the liquid phase method is advantageous in that good reactivity is exhibited, and intermediate peptide can be purified by extraction and washing, isolation, and the like after a condensation reaction. However, the liquid phase method still has problems in each step of coupling reaction and deprotection.

As a protective group-forming reagent in the related art, a xanthene compound disclosed in WO2018/021233A and a diphenylmethane compound disclosed in WO2010/113939A have been known.

SUMMARY OF THE INVENTION

WO2018/021233A only discloses a xanthene compound which is difficult to precipitate in an organic solvent and can be easily separated and purified by a liquid-liquid phase separation operation, and there is no disclosure or suggestion of a protective group using a xanthene compound suitable for a solid-liquid phase separation.

An object to be achieved by an embodiment of the present disclosure is to provide a method for producing a peptide compound having an excellent deprotection rate and temporal stability.

An object to be achieved by another embodiment of the present disclosure is to provide a protective group-forming reagent having an excellent deprotection rate and temporal stability.

An object to be achieved by still another embodiment of the present disclosure is to provide a novel condensed polycyclic compound.

The methods for achieving the above-described objects include the following aspects.

<1> A method for producing a peptide compound, comprising:
a step of using a compound represented by Formula (1).

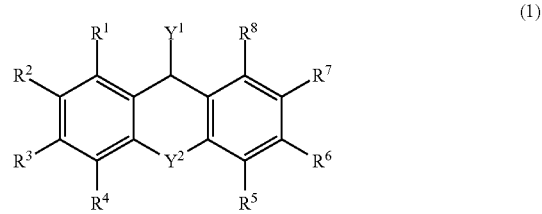

In Formula (1),
$Y^1$ represents $-OR^{17}$, $-NHR^{18}$, $-SH$, or a halogen atom, where $R^{17}$ represents a hydrogen atom, an active ester-type carbonyl group, or an active ester-type sulfonyl group, and $R^{18}$ represents a hydrogen atom, an alkyl group, an arylalkyl group, a heteroarylalkyl group, or a 9-fluorenylmethoxycarbonyl group,
$Y^2$ represents $-N(R^{110})-$, $-O-$, $-S-$, $-CR^{100}=CR^{101}-$, $-CR^{102}R^{103}-CR^{104}R^{105}-$, or $-CR^{106}R^{107}-$, where $R^{110}$ represents $R^A$ or an alkyl group, and $R^{100}$ to $R^{107}$ each independently represent a hydrogen atom or an alkyl group,
$R^1$ to $R^8$ each independently represent $R^A$, a hydrogen atom, a halogen atom, an alkyl group, or an alkoxy group,
at least one of $R^1$ to $R^8$ or $Y^2$ has $R^A$,
$R^A$ represents an aliphatic hydrocarbon group or an organic group having an aliphatic hydrocarbon group,
in a case where only one $R^A$ is present, the number of carbon atoms in the aliphatic hydrocarbon group of $R^A$ is 12 or more, and
in a case where a plurality of $R^A$'s are present, the number of carbon atoms in at least one aliphatic hydrocarbon group of $R^A$ is 12 or more,
provided that, $R^A$ does not have a silyl group and a hydrocarbon group having a silyloxy structure.
<2> The method for producing a peptide compound according to <1>,
in which the step of using the compound represented by Formula (1) is a C-terminal protecting step of protecting a carboxy group or an amide group of an amino acid compound or a peptide compound with the compound represented by Formula (1).
<3> The method for producing a peptide compound according to <2>,
in which the amino acid compound or the peptide compound in the C-terminal protecting step is an N-terminal protected amino acid compound or an N-terminal protected peptide compound.
<4> The method for producing a peptide compound according to <3>, further comprising:
an N-terminal deprotecting step of deprotecting an N-terminal end of an N-terminal and C-terminal protected amino acid compound or an N-terminal and C-terminal protected peptide compound, which is obtained in the C-terminal protecting step; and
a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound.

<5> The method for producing a peptide compound according to <4>, further comprising:
a precipitating step of precipitating an N-terminal and C-terminal protected peptide compound obtained in the peptide chain extending step.

<6> The method for producing a peptide compound according to <5>, further comprising, one or more times in the following order after the precipitating step:
a step of deprotecting the N-terminal end of the obtained N-terminal and C-terminal protected peptide compound;
a step of condensing the N-terminal end of the obtained C-terminal protected peptide compound with an N-terminal protected amino acid compound or an N-terminal protected peptide compound; and
a step of precipitating the obtained N-terminal and C-terminal protected peptide compound.

<7> The method for producing a peptide compound according to any one of <1> to <6>, further comprising:
a C-terminal deprotecting step of deprotecting a C-terminal protective group.

<8> The method for producing peptide compound according to any one of <1> to <7>,
in which a total number of carbon atoms in all aliphatic hydrocarbon groups included in all $R^4$'s is 18 or more.

<9> The method for producing a peptide compound according to any one of <1> to <8>,
in which a total number of carbon atoms in all aliphatic hydrocarbon groups included in all $R^4$'s is 36 to 80.

<10> The method for producing peptide according to any one of <1> to <9>, wherein at least one of $R^3$ or $R^6$ in Formula (1) is $R^4$.

<11> The method for producing a peptide compound according to any one of <1> to <10>,
in which $R^4$'s are each independently a group represented by Formula (f1) or Formula (a1).

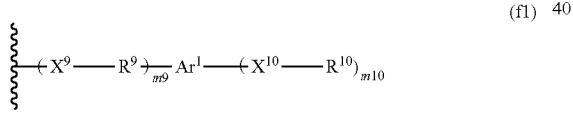

(f1)

In Formula (f1), a wavy line portion represents a bonding position to other configurations, m9 represents an integer of 1 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms.

(a1)

In Formula (a1), a wavy line portion represents a bonding position to other configurations, m20 represents an integer of 1 to 10, $X^{20}$'s each independently represent a single bond, —O—, —S—, —COO—, —OCO—, —OCONH—, —NHCONH—, —NHCO—, or —CONH—, and at least one of $R^{20}$'s is a divalent aliphatic hydrocarbon group having 5 or more carbon atoms.

<12> The method for producing a peptide compound according to <11>,
in which the group represented by Formula (f1) is a group represented by Formula (f2).

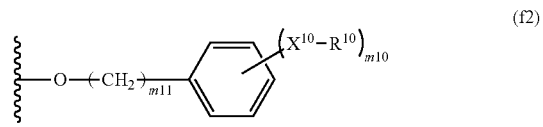

(f2)

In Formula (f2), a wavy line portion represents a bonding position to other configurations, m10 represents an integer of 1 to 3, m11 represents an integer of 1 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms.

<13> The method for producing a peptide compound according to <11>,
in which $X^{20}$ in Formula (a1), which is bonded to the other configurations, is —O—.

<14> A protective group-forming reagent comprising:
a compound represented by Formula (1).

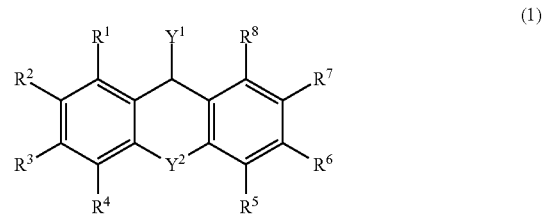

(1)

In Formula (1),
$Y^1$ represents —$OR^{17}$, —$NHR^8$, —SH, or a halogen atom, where $R^{17}$ represents a hydrogen atom, an active ester-type carbonyl group, or an active ester-type sulfonyl group, and $R^{18}$ represents a hydrogen atom, an alkyl group, an arylalkyl group, a heteroarylalkyl group, or a 9-fluorenylmethoxycarbonyl group,
$Y^2$ represents —$N(R^{110})$—, —O—, —S—, —$CR^{100}$=$CR^{101}$—, —$CR^{102}R^{103}$—$CR^{104}R^{105}$—, or —$CR^{106}R^{107}$—, where $R^{110}$ represents $R^4$ or an alkyl group, and $R^{100}$ to $R^{107}$ each independently represent a hydrogen atom or an alkyl group,
$R^1$ to $R^8$ each independently represent $R^4$, a hydrogen atom, a halogen atom, an alkyl group, or an alkoxy group,
at least one of $R^1$ to $R^8$ or $Y^2$ has $R^4$,
$R^4$ represents an aliphatic hydrocarbon group or an organic group having an aliphatic hydrocarbon group, and
the number of carbon atoms in at least one aliphatic hydrocarbon group of $R^4$ is 12 or more, provided that, $R^A$ does not have a silyl group and a hydrocarbon group having a silyloxy structure.

<15> The protective group-forming reagent according to <14>,
in which the protective group-forming reagent is a protective group-forming reagent of a carboxy group or an amide group.

<16> The protective group-forming reagent according to <14> or <15>,
in which the protective group-forming reagent is a C-terminal protective group-forming reagent of an amino acid compound or a peptide compound.

<17> A condensed polycyclic compound represented by Formula (1a).

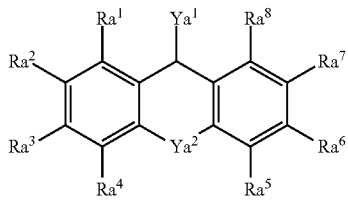

In Formula (1a),
$Ya^1$ represents $-ORa^{17}$, $-NHRa^{18}$, $-SH$, or a halogen atom, where $Ra^{17}$ represents a hydrogen atom, an active ester-type carbonyl group, or an active ester-type sulfonyl group, and $Ra^{18}$ represents a hydrogen atom, a linear or branched alkyl group having 10 or less carbon atoms, an arylalkyl group, a heteroarylalkyl group, or a 9-fluorenylmethoxycarbonyl group,
$Ya^2$ represents $-N(R^{110})-$, $-O-$, $-S-$, $-CRa^{100}=CRa^{101}-$, $-CRa^{102}Ra^{103}-CRa^{104}Ra^{105}-$, or $-CRa^{106}Ra^{107}-$, where $R^{110}$ represents $R^A$ or an alkyl group, and $Ra^{100}$ to $Ra^{107}$ each independently represent a hydrogen atom or an alkyl group,
$Ra^1$ to $Ra^8$ each independently represent $R^A$, a hydrogen atom, a halogen atom, an alkyl group having 1 to 4 carbon atoms, or an alkoxy group having 1 to 4 carbon atoms,
at least one of $Ra^2$, . . . , or $Ra^7$ has $R^A$
$R^A$ represents an aliphatic hydrocarbon group or an organic group having an aliphatic hydrocarbon group, and
the number of carbon atoms in at least one aliphatic hydrocarbon group of $R^A$ is 12 or more,
provided that, $R^A$ does not have a silyl group and a hydrocarbon group having a silyloxy structure.

<18> The condensed polycyclic compound according to <17>,
in which at least one of $R^3$ or $R^6$ in Formula (1a) is $R^A$.

<19> The condensed polycyclic compound according to <17> or <18>,
in which $R^A$'s in Formula (1a) are each independently a group represented by Formula (f1) or Formula (a1).

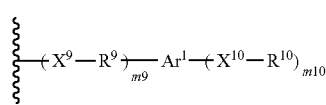

In Formula (f1), a wavy line portion represents a bonding position to other configurations, m9 represents an integer of 1 to 3, $X^9$'s each independently represent a single bond, $-O-$, $-S-$, $-COO-$, $-OCO-$, $-OCONH-$, $-NHCONH-$, $-NHCO-$, or $-CONH-$, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, $-O-$, $-S-$, $-COO-$, $-OCO-$, $-OCONH-$, $-NHCONH-$, $-NHCO-$, or $-CONH-$, $R^{10}$'s each independently represent a monovalent aliphatic hydrocarbon group, and at least one of $R^{10}$'s is a monovalent aliphatic hydrocarbon group having 5 or more carbon atoms.

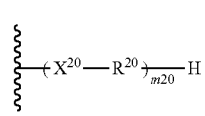

In Formula (a1), a wavy line portion represents a bonding position to other configurations, m20 represents an integer of 1 to 10, $X^{20}$'s each independently represent a single bond, $-O-$, $-S-$, $-COO-$, $-OCO-$, $-OCONH-$, $-NHCONH-$, $-NHCO-$, or $-CONH-$, and at least one of $R^{20}$'s is a divalent aliphatic hydrocarbon group having 5 or more carbon atoms.

<20> The condensed polycyclic compound according to <19>,
in which the group represented by Formula (f1) is a group represented by Formula (f2).

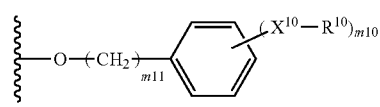

In Formula (f2), a wavy line portion represents a bonding position to other configurations, m10 represents an integer of 1 to 3, m11 represents an integer of 1 to 3, $X^{10}$'s each independently represent a single bond, $-O-$, $-S-$, $-COO-$, $-OCO-$, $-OCONH-$, $-NHCONH-$, $-NHCO-$, or $-CONH-$, and $R^{10}$'s each independently represent a monovalent aliphatic hydrocarbon group having 5 or more carbon atoms.

<21> The condensed polycyclic compound according to <19>,
in which $X^{20}$ in Formula (a1), which is bonded to the other configurations, is $-O-$.

According to an embodiment of the present invention, it is possible to provide a method for producing a peptide compound having an excellent deprotection rate and temporal stability.

In addition, according to another embodiment of the present invention, it is possible to provide a protective group-forming reagent having an excellent deprotection rate and temporal stability.

In addition, according to still another embodiment of the present invention, it is possible to provide a novel condensed polycyclic compound.

DESCRIPTION OF THE PREFERRED EMBODIMENTS

Hereinafter, the contents of the present disclosure will be described in detail. The description of configuration requirements below is made based on representative embodiments of the present disclosure in some cases, but the present disclosure is not limited to such embodiments.

In the present specification, unless otherwise specified, each term has the following meaning. A numerical range represented using "to" means a range including numerical values described before and after the preposition "to" as a lower limit value and an upper limit value.

In numerical ranges described in stages in the present specification, an upper limit value or a lower limit value described in one numerical range may be replaced with an upper limit value or a lower limit value of a numerical range described in another stage. In addition, in the numerical ranges described in the present specification, the upper limit value or the lower limit value of the numerical ranges may be replaced with the values shown in examples.

The term "step" includes not only the independent step but also a step in which intended purposes are achieved even in a case where the step cannot be precisely distinguished from other steps.

In a case where substitution or unsubstitution is not noted in regard to the notation of a "group" (atomic group), the "group" includes not only a group not having a substituent but also a group having a substituent. For example, the concept of an "alkyl group" includes not only an alkyl group not having a substituent (unsubstituted alkyl group) but also an alkyl group having a substituent (substituted alkyl group).

A chemical structural formula may be described by a simplified structural formula in which hydrogen atoms are omitted.

"% by mass" has the same definition as that for "% by weight", and "part by mass" has the same definition as that for "part by weight".

A combination of two or more preferred aspects is a more preferred aspect.

The alkyl group may be chain-like or branched, and may be substituted with a halogen atom or the like. Examples of an alkyl group having 1 to 6 carbon atoms (also referred to as "the number of carbon atoms") include methyl, ethyl, propyl, isopropyl, butyl, and tert-butyl.

Examples of an alkenyl group having 2 to 6 carbon atoms include 1-propenyl.

As an aryl group, an aryl group having 6 to 14 carbon atoms is preferable, and examples thereof include a phenyl group, a 1-naphthyl group, a 2-naphthyl group, a biphenylyl group, and a 2-anthryl group. Among these, an aryl group having 6 to 10 carbon atoms is more preferable, and a phenyl group is particularly preferable.

Examples of a silyl group include trimethylsilyl, triethylsilyl, dimethylphenylsilyl, tert-butyldimethylsilyl, and tert-butyldiethylsilyl.

Examples of a halogen atom include a fluorine atom, a chlorine atom, a bromine atom, and an iodine atom.

Examples of an alkoxy group having 1 to 6 carbon atoms include methoxy, ethoxy, and propoxy.

Examples of an aralkyl group having 7 to 10 carbon atoms include benzyl.

Examples of an acyl group having 1 to 6 carbon atoms include acetyl and propionyl.

Examples of an aralkyl-carbonyl group having 7 to 10 carbon atoms include benzylcarbonyl.

Examples of an alkoxycarbonyl group having 1 to 6 carbon atoms include methoxycarbonyl, ethoxycarbonyl, and a Boc group. The Boc group means a tert-butoxycarbonyl group.

Examples of an aralkyloxycarbonyl group having 7 to 14 carbon atoms include benzyloxycarbonyl and an Fmoc group. The Fmoc group means a 9-fluorenylmethoxycarbonyl group.

(Method for Producing Peptide Compound)

A method for producing a peptide compound according to an embodiment of the present disclosure includes a step of using a compound represented by Formula (1).

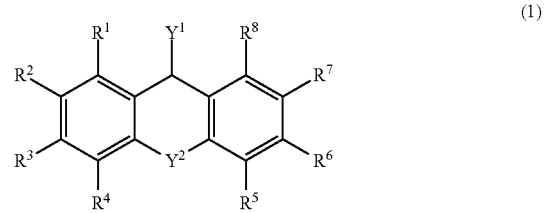

In Formula (1), $Y^1$ represents —$OR^{17}$, —$NHR^{18}$, —SH, or a halogen atom, where $R^{17}$ represents a hydrogen atom, an active ester-type carbonyl group, or an active ester-type sulfonyl group, and $R^{18}$ represents a hydrogen atom, a linear or branched alkyl group having 1 to 6 carbon atoms, an arylalkyl group, a heteroarylalkyl group, or a 9-fluorenylmethoxycarbonyl group (hereinafter, also referred to as an Fmoc group), $Y^2$ represents —$N(R^{110})$—, —O—, —S—, —$CR^{100}$=$CR^{101}$—, —$CR^{102}R^{103}$—$CR^{104}R^{105}$—, or —$CR^{106}R^{107}$—, where $R^{110}$ represents $R^A$ or an alkyl group, and $R^{100}$ to $R^{107}$ each independently represent a hydrogen atom or an alkyl group, $R^1$ to $R^8$ each independently represent $R^A$, a hydrogen atom, a halogen atom, an alkyl group having 1 to 4 carbon atoms, or an alkoxy group having 1 to 4 carbon atoms, at least one of $R^1$ to $R^8$ or $Y^2$ has $R^A$, $R^A$ represents an aliphatic hydrocarbon group or an organic group having an aliphatic hydrocarbon group, in a case where only one $R^A$ is present, the number of carbon atoms in the aliphatic hydrocarbon group of $R^A$ is 12 or more, and in a case where a plurality of $R^A$'s are present, the number of carbon atoms in at least one aliphatic hydrocarbon group of $R^A$ is 12 or more, provided that, $R^A$ does not have a silyl group and a hydrocarbon group having a silyloxy structure.

According to an embodiment of the present disclosure, it is possible to provide a method for producing a peptide compound having an excellent yield. In particular, it is possible to provide a method for producing a peptide compound having an excellent deprotection rate and temporal stability. The detailed mechanism for obtaining the above-described effect is not clear, but assumed as follows.

The excellent temporal stability means that the condensed polycyclic compound represented by Formula (1) according to the present disclosure does not decompose during storage, or that a compound protected by the condensed polycyclic compound represented by Formula (1) according to the present disclosure does not deprotect and decompose under conditions other than deprotection conditions.

Since the compound represented by Formula (1) according to the present disclosure has at least one aliphatic hydrocarbon group having 12 or more carbon atoms, a compound to be protected has excellent solubility in a hydrophobic solvent. Furthermore, with regard to a hydrophilic solvent, since the aliphatic hydrocarbon groups in $R^4$ aggregate with each other and the compound represented by Formula (1) has a condensed polycyclic structure, in the obtained peptide compound, stacking interaction between condensed polycyclic structures occurs, so that crystallization property is excellent and purification and separability are also excellent.

In other words, in a case where the compound protected by Formula (1) is subjected to a reaction, since the compound has excellent solubility in a hydrophobic solvent as a reaction solvent, it is presumed that the reaction proceeds rapidly, and since a target product is efficiently crystallized and purified by adding a polar solvent which is a poor solvent during purification, it is presumed that it is suitable for a solid-liquid phase separation, and yield of the obtained compound (peptide compound and the like) is excellent.

In addition, it is presumed that a compound protected by the compound represented by Formula (1) according to the present disclosure has a high deprotection rate, so that side reactions are suppressed and the yield of the obtained peptide compound or the like is excellent. The reason why the deprotection rate is excellent is presumed that, as compared with the diphenylmethane-type compound disclosed in WO2010/113939A, since the compound represented by Formula (1) has the condensed polycyclic structure and has $Y^2$ of an electron-donating substituent, electron density of a carbon atom to which $Y^1$ is linked is improved, so that the deprotection rate is excellent.

Since the compound represented by Formula (1) according to the present disclosure and the compound protected by the compound represented by Formula (1) are an aliphatic hydrocarbon group not having the silyloxy structure disclosed in WO2018/021233A, it is presumed that the compounds are solid at normal temperature and are inferior in intermolecular reactivity, so that the storage stability is excellent, formation of by-product is suppressed, resulting in excellent yield.

In WO2018/021233A in which a protective group suitable for the liquid-liquid phase separation is disclosed, there is no disclosure or suggestion of changing a hydrocarbon group having a silyloxy structure, which is the protective group suitable for the liquid-liquid phase separation, to an aliphatic hydrocarbon group having 12 or more carbon atoms. In addition, there is no motivation to change a tag of the liquid-liquid phase separation from a silyl group to an alkyl group.

In particular, storage stability of pharmaceutical raw materials is important for quality control (GMP) in pharmaceutical production. Since the compound represented by Formula (1) according to the present disclosure and the compound protected by the compound represented by Formula (1) are excellent in storage stability, the compounds can be particularly suitably used for pharmaceutical production.

From the above, in the compound protected by the compound represented by Formula (1) according to the present disclosure, both deprotection rate and temporal stability can be achieved. In the present specification, it can be said that, as the deprotection rate is high, the deprotection rate is excellent.

Furthermore, even poorly synthesized peptides such as unnatural peptide including unnatural amino acid, in which a side reaction is likely to occur, the peptide can be synthesized with high purity due to suppression of the side reaction.

In the production method according to the embodiment of the present disclosure, a C-terminal protective group can be deprotected even under weak acid conditions, and a side reaction of the obtained peptide can be suppressed. Therefore, the production method according to the embodiment of the present disclosure is suitable for the synthesis of acid-sensitive peptides, for example, peptides having an N-alkylamide structure.

Hereinafter, the method for producing a peptide compound according to the embodiment of the present disclosure will be described in detail.

In the method for producing a peptide compound according to the embodiment of the present disclosure, the compound represented by Formula (1) can be used not only for formation of a protective group, but also for denaturation of a peptide compound, adjustment of solubility in water or an organic solvent, improvement of crystallinity, multimerization, and the like.

Among these, the compound represented by Formula (1) is preferably used for formation of a protective group, and more preferably used for forming a C-terminal protective group in an amino acid compound or a peptide compound.

<Condensed Polycyclic Aromatic Hydrocarbon Compound Represented by Formula (1)>

The compound represented by Formula (1) according to the present disclosure will be described below in detail.

[$Y^1$]

$Y^1$ in Formula (1) represents $-OR^{17}$, $-NHR^{18}$, $-SH$, or a halogen atom, where $R^{17}$ represents a hydrogen atom, an active ester-type carbonyl group, or an active ester-type sulfonyl group, and $R^{18}$ represents a hydrogen atom, a linear or branched alkyl group having 1 to 6 carbon atoms, an arylalkyl group, or a heteroarylalkyl group.

As the halogen atom, from the viewpoint of reaction yield and storage stability, a bromine atom or a chlorine atom is preferable.

Examples of the active ester-type carbonyl group in $R^{17}$ include carbonyloxysuccinate imide, an alkoxycarbonyl group, an aryloxycarbonyl group, and an aralkyloxycarbonyl group, and from the viewpoint of deprotection rate and temporal stability, preferred examples thereof include carbonyloxysuccinate imide.

Examples of the active ester-type sulfonyl group in $R^{17}$ include an alkylsulfonyl group and an arylsulfonyl group, and from the viewpoint of deprotection rate and temporal stability, preferred examples thereof include an alkylsulfonyl group having 1 to 6 carbon atoms and an p-toluenesulfonyl group.

Among these, $R^{17}$ is preferably a hydrogen atom or an active ester-type protective group, and more preferably a hydrogen atom.

Examples of the alkyl group in $R^{18}$ include an alkyl group having 1 to 30 carbon atoms, and an alkyl group having 1 to 10 carbon atoms is preferable and an alkyl group having 1 to 6 carbon atoms is more preferable. Among these, more preferred examples thereof include a methyl group and an ethyl group.

Examples of the arylalkyl group in $R^{18}$ include an arylalkyl group having 7 to 30 carbon atoms, and an arylalkyl group having 7 to 20 carbon atoms is preferable and an aralkyl group having 7 to 16 carbon atoms (for example, a group in which an alkylene group having 1 to 6 carbon atoms is bonded to an aryl group having 6 to 10 carbon atoms) is more preferable. Suitable specific examples thereof include a benzyl group, a 1-phenylethyl group, a 2-phenylethyl group, a 1-phenylpropyl group, a naphthylmethyl group, a 1-naphthylethyl group, and a 1-naphthylpropyl group, and a benzyl group is more preferable.

Examples of the heteroarylalkyl group in $R^{18}$ include a heteroarylalkyl group having 5 to 30 carbon atoms, and a heteroarylalkyl group having 5 to 20 carbon atoms is preferable and a heteroarylalkyl group having 5 to 16 carbon atoms (for example, a group in which an alkylene group having 1 to 6 carbon atoms is bonded to a heteroaryl group having 4 to 10 carbon atoms) is more preferable. Suitable specific examples thereof include an indolylmethyl group, a furfuryl group, a benzofuranylmethyl group, a thiophenylmethyl group, and a benzothiophenylmethyl group.

Among these, from the viewpoint of deprotection rate and temporal stability, $R^{18}$ is preferably a hydrogen atom, an alkyl group having 1 to 6 carbon atoms, an arylalkyl group having 7 to 16 carbon atoms, or an Fmoc group, more preferably a hydrogen atom, a methyl group, an ethyl group, a benzyl group, or an Fmoc group, and still more preferably a hydrogen atom or an Fmoc group. In a case where $R^{18}$ is an Fmoc group, since $Y^4$ becomes $-NH_2$ by deprotecting the Fmoc group with a base such as DBU described later, it can be considered that the case where $R^{18}$ is an Fmoc group and the case where $R^{18}$ is a hydrogen atom are equivalent.

From the viewpoint of deprotection rate and temporal stability, as $Y^1$, $-OR^{17}$ ($R^{17}$ is a hydrogen atom or an active ester-type protective group), $-NHR^{18}$ ($R^{18}$ is a hydrogen atom, a linear or branched alkyl group having 1 to 6 carbon atoms, an aralkyl group, or an Fmoc group), or a halogen atom is preferable, $-OR^{17}$ ($R^{17}$ is a hydrogen atom or an active ester-type protective group) or $-NHR^{18}$ ($R^{18}$ is a hydrogen atom, a linear or branched alkyl group having 1 to 6 carbon atoms, or an Fmoc group) is more preferable, and $-NHR^{18}$ ($R^{18}$ is a hydrogen atom or a linear or branched alkyl group having 1 to 6 carbon atoms) is still more preferable.

[$Y^2$]

$Y^2$ represents $-N(R^{110})-$, $-O-$, $-S-$, $-CR^{100}=CR^{101}-$, $-CR^{102}R^{103}-CR^{104}R^{105}-$, or $-CR^{106}R^{107}-$.

$R^{110}$ is preferably $R^A$. $R^A$ has the meaning as $R^A$ which will be described later, and the preferred aspects thereof are also the same.

As the alkyl group in $R^{100}$ to $R^{107}$, an alkyl group having 1 to 5 carbon atoms is preferable, an alkyl group having 1 to 3 carbon atoms is more preferable, and an alkyl group having 1 or 2 carbon atoms is still more preferable.

$R^{100}$ and $R^{101}$ in $-CR^{100}=CR^{101}-$ preferably have the same group, and are more preferably an alkyl group having 1 to 5 carbon atoms or a hydrogen atom, still more preferably an alkyl group having 1 to 3 carbon atoms or a hydrogen atom, particularly preferably an alkyl group having 1 or 2 carbon atoms or a hydrogen atom, and it is most preferable that both $R^{100}$ and $R^{101}$ are a hydrogen atom.

Specific examples thereof include $-CH=CH-$ and $-C(CH_3)=C(CH_3)-$.

$R^{102}$ to $R^{105}$ in $-CR^{102}R^{103}-CR^{104}R^{105}-$ may be different from each other, but it is preferable that $R^{102}$ and $R^{104}$, and $R^{103}$ and $R^{105}$ are the same groups, respectively.

As $R^{102}$ and $R^{104}$, an alkyl group having 1 to 5 carbon atoms or a hydrogen atom is more preferable, an alkyl group having 1 to 3 carbon atoms or a hydrogen atom is still more preferable, an alkyl group having 1 or 2 carbon atoms or a hydrogen atom is particularly preferable, and it is most preferable that both are a hydrogen atom.

As $R^{103}$ and $R^{105}$, an alkyl group having 1 to 5 carbon atoms or a hydrogen atom is more preferable, an alkyl group having 1 to 3 carbon atoms or a hydrogen atom is still more preferable, an alkyl group having 1 or 2 carbon atoms or a hydrogen atom is particularly preferable, and it is most preferable that both are a hydrogen atom.

Specific examples thereof include $-CH_2-CH_2-$.

$R^{106}$ and $R^{107}$ in $-CR^{106}R^{107}-$ preferably has the same group, and are more preferably an alkyl group having 1 to 5, still more preferably an alkyl group having 1 to 3 carbon atoms, and particularly preferably an alkyl group having 1 or 2 carbon atoms.

Specific examples thereof include $-CH_2-$, $-C(CH_3)_2-$, and $-C(C_2H_5)_2-$.

From the viewpoint of deprotection rate and temporal stability, as $Y^2$, $-O-$, $-S-$, $-CR^{100}=CR^{101}-$, $-CR^{102}R^{103}-CR^{104}R^{105}-$, or $-CR^{106}R^{107}-$ is preferable, an oxygen atom ($-O-$) or a sulfur atom ($-S-$) is more preferable, and an oxygen atom ($-O-$) is still more preferable.

[$R^1$ to $R^8$]

$R^1$ to $R^8$ each independently represent $R^A$, a hydrogen atom, a halogen atom, an alkyl group having 1 to 4 carbon atoms, or an alkoxy group having 1 to 4 carbon atoms, where at least one of $R^1$ to $R^8$ or $Y^2$ has $R^A$, and $R^A$ represents an aliphatic hydrocarbon group or an organic group having an aliphatic hydrocarbon group. In a case where only one $R^A$ is present in the compound, the number of carbon atoms in the aliphatic hydrocarbon group is 12 or more, and in a case where a plurality of $R^A$'s are present in the compound, the number of carbon atoms in at least one aliphatic hydrocarbon group is 12 or more. However, $R^A$ does not have a silyl group and a hydrocarbon group having a silyloxy structure. It is preferable that only one of $R^1$, . . . , or $R^5$ is $R^A$, it is more preferable that only $R^3$ or $R^6$ is $R^A$, and it is still more preferable that $R^1$ to $R^5$, and $R^7$ and $R^8$ are each independently a hydrogen atom, a halogen atom, an alkyl group, or an alkoxy group, and $R^3$ or $R^6$ is $R^A$.

As $R^1$ to $R^8$, $R^A$, a hydrogen atom, a fluorine atom, a chlorine atom, a methyl group, or an alkoxy group is preferable, and $R^A$, a hydrogen atom, a fluorine atom, or a chlorine atom is more preferable.

In the present specification, the "organic group having an aliphatic hydrocarbon group" in $R^A$ is a monovalent (one bonding site bonded to the ring A) organic group having an aliphatic hydrocarbon group in its molecular structure.

The "aliphatic hydrocarbon group" in the "organic group having an aliphatic hydrocarbon group" is a linear, branched, or cyclic saturated or unsaturated aliphatic hydrocarbon group, and an aliphatic hydrocarbon group having 5 or more carbon atoms is preferable, an aliphatic hydrocarbon group having 5 to 60 carbon atoms is more preferable, an aliphatic hydrocarbon group having 5 to 30 carbon atoms is still more preferable, and an aliphatic hydrocarbon group having 10 to 30 carbon atoms is particularly preferable.

The moiety of the "aliphatic hydrocarbon group" in the "organic group having an aliphatic hydrocarbon group" is not particularly limited, and may be present at the terminal (a monovalent group) or may be present at any other site (for example, a divalent group).

Examples of the "aliphatic hydrocarbon group" include an alkyl group, a cycloalkyl group, an alkenyl group, and an alkynyl group, and specific examples thereof include monovalent groups such as a pentyl group, a hexyl group, an octyl group, a decyl group, a hexadecyl group, an octadecyl group, an icosyl group, a docosyl group, a tetracosyl group, a lauryl group, a tridecyl group, a myristyl group, an oleyl group, and an isostearyl group; divalent groups derived from these (divalent groups obtained by removing one hydrogen atom from the monovalent groups); and groups removing a hydroxyl group or the like from various steroid groups.

As the "alkyl group", for example, an alkyl group having 5 to 30 carbon atoms or the like is preferable, and examples thereof include a pentyl group, a hexyl group, an octyl group, a decyl group, a hexadecyl group, an octadecyl group, an icosyl group, a docosyl group, a tetracosyl group, a lauryl group, a tridecyl group, a myristyl group, and an isostearyl group. Among these, an octadecyl group, an icosyl group, a docosyl group, or a tetracosyl group is preferable, and an icosyl group, a docosyl group, or a tetracosyl group is more preferable.

As the "cycloalkyl group", for example, a cycloalkyl group having 5 to 30 carbon atoms, or the like is preferable, and examples thereof include a cyclopentyl group, a cyclohexyl group, an isobornyl group, and a tricyclodecanyl group. In addition, these may be linked repeatedly, or may be a condensed structure of two or more rings.

As the "alkenyl group", for example, an alkenyl group having 5 to 30 carbon atoms, or the like is preferable, and examples thereof include a vinyl group, a 1-propenyl group, an allyl group, an isopropenyl group, a butenyl group, and an isobutenyl group.

As the "alkynyl group", for example, an alkynyl group having 5 to 30 carbon atoms or the like is preferable, and examples thereof include a 4-pentynyl group and a 5-hexenyl group.

As the "steroid group", for example, cholesterol, estradiol, or the like is preferable.

A moiety other than the "aliphatic hydrocarbon group" in the "organic group having an aliphatic hydrocarbon group" can be optionally set. For example, the "organic group having an aliphatic hydrocarbon group" may have a moiety such as —O—, —S—, —COO—, —OCONH—, —CONH—, and a hydrocarbon group (monovalent group or divalent group) other than the "aliphatic hydrocarbon group".

Examples of the "hydrocarbon group" other than the "aliphatic hydrocarbon group" include an aromatic hydrocarbon group, and specifically, for example, a monovalent group such as an aryl group or a divalent group derived from the monovalent group is used.

In addition, the above-described aliphatic hydrocarbon group and the hydrocarbon group other than the above-described aliphatic hydrocarbon group may be substituted with a substituent selected from a halogen atom, an oxo group, and the like.

The bond (substitution) of $R^1$ to $R^8$ of the "organic group having an aliphatic hydrocarbon group" to the ring A may be through the above-described "aliphatic hydrocarbon group" or the above-described "hydrocarbon group" existing in $R^A$, that is, may be directly bonded by a carbon-carbon bond, or may be through a moiety such as —O—, —S—, —COO—, —OCONH—, and —CONH—, which exists in $R^A$. From the viewpoint of ease of synthesizing the compound, the bond (substitution) of $R^1$ to $R^8$ is preferably through —O—, —S—, —COO—, or —CONH—, and particularly preferably through —O—.

From the viewpoint of ease of compound synthesis, it is preferable that the bond (substitution) of the "organic group having an aliphatic hydrocarbon group" to N in $Y^2$ is through the "hydrocarbon group" existing in $R^A$ described above, that is, directly bonded by a carbon-nitrogen bond.

In the compound represented by Formula (1) according to the present disclosure, from the viewpoint of deprotection rate and temporal stability, in a case where only one $R^A$ is present, the total number of carbon atoms in all aliphatic hydrocarbon groups included in $R^A$ is preferably 18 or more, more preferably 24 to 200, still more preferably 32 to 100, particularly preferably 34 to 80, and most preferably 36 to 80. In addition, in a case where in a case where a plurality of $R^A$'s are present, the number of carbon atoms in all aliphatic hydrocarbon groups included in all $R^A$'s is preferably 18 or more, more preferably 24 to 200, still more preferably 32 to 100, particularly preferably 34 to 80, and most preferably 36 to 80.

In addition, the compound represented by Formula (1) according to the present disclosure is a compound which has at least one aliphatic hydrocarbon group having 12 or more carbon atoms in at least one $R^A$. A compound which has at least one aliphatic hydrocarbon group having 12 to 100 carbon atoms in at least one $R^A$ is preferable, a compound which has at least one aliphatic hydrocarbon group having 18 to 40 carbon atoms in at least one $R^A$ is more preferable, and a compound which has at least one aliphatic hydrocarbon group having 20 to 36 carbon atoms in at least one $R^A$ is still more preferable.

Furthermore, from the viewpoint of temporal stability, the above-described aliphatic hydrocarbon group is preferably an alkyl group and more preferably a linear alkyl group.

In addition, the number of carbon atoms in one $R^A$ is preferably 12 to 200, more preferably 18 to 150, still more preferably 18 to 100, and particularly preferably 20 to 80, respectively.

In the above-described compound represented by Formula (1), from the viewpoint of deprotection rate and temporal stability, it is preferable that at least one of $R^1, \ldots,$ or $R^8$ is $R^A$, it is more preferable that at least one of $R^2, \ldots, R^7$ is $R^A$, it is still more preferable that at least one selected from the group consisting of $R^2, R^3, R^6,$ and $R^7$ is $R^A$, it is particularly preferable that any one of $R^3$ or $R^6$ is $R^A$, and it is most preferable that $R^3$ or $R^6$ is $R^A$.

In Formula (1), from the viewpoint of deprotection rate and temporal stability, it is preferable that at least one $R^A$ is a group represented by any of Formula (f1), Formula (a1), Formula (b1), or Formula (e1), it is more preferable to be a group represented by Formula (f1) or Formula (a1), and it is particularly preferable to be a group represented by Formula (f1).

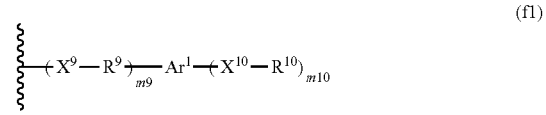

(f1)

In Formula (f1), a wavy line portion represents a bonding position to other configurations, m9 represents an integer of 1 to 3, $X^9$'s each independently represent a single bond, —O—, —S—, —COO—, —OCO—, —OCONH—, —NHCONH—, —NHCO—, or —CONH—, $R^9$'s each independently represent a divalent aliphatic hydrocarbon group, $Ar^1$ represents an (m10+1)-valent aromatic group or an (m10+1)-valent heteroaromatic group, m10 represents an integer of 1 to 3, $X^{10}$'s each independently represent a single bond, —O—, —S—, —COO—, —OCO—, —OCONH—, —NHCONH—, —NHCO—, or —CONH—, $R^{10}$'s each independently represent a monovalent aliphatic hydrocarbon group, and at least one of $R^{10}$'s is a monovalent aliphatic hydrocarbon group having 5 or more carbon atoms.

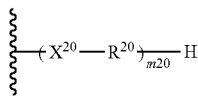
(a1)

In Formula (a1), a wavy line portion represents a bonding position to other configurations, m20 represents an integer of 1 to 10, $X^{20}$'s each independently represent a single bond, —O—, —S—, —COO—, —OCO—, —OCONH—, —NHCONH—, —NHCO—, or —CONH—, and at least one of $R^{20}$'s is a divalent aliphatic hydrocarbon group having 5 or more carbon atoms.

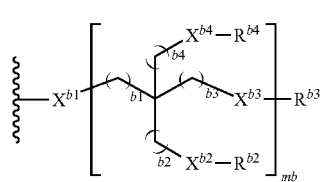
(b1)

In Formula (b1), a wavy line portion represents a bonding position to other configurations, mb represents 1 or 2, b1 to b4 each independently represent an integer of 0 to 2, $X^{b1}$ to $X^{b4}$ each independently represent a single bond, —O—, —S—, —COO—, —OCONH—, or —CONH—, $R^{b2}$ and $R^{b4}$ each independently represent a hydrogen atom, a methyl group, or an aliphatic hydrocarbon group having 5 or more carbon atoms, and $R^{b3}$ represents an aliphatic hydrocarbon group having 5 or more carbon atoms.

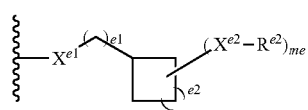
(e1)

In Formula (e1), a wavy line portion represents a bonding position to other configurations, $X^{e1}$ represents a single bond, —O—, —S—, —NHCO—, or —CONH—, me represents an integer of 0 to 15, e1 represents an integer of 0 to 11, e2 represents an integer of 0 to 5, $X^{e2}$'s each independently represent a single bond, —O—, —S—, —COO—, —OCONH—, —NHCO—, or —CONH—, and $R^{e2}$'s each independently represent a hydrogen atom, a methyl group, or an organic group having an aliphatic hydrocarbon group having 5 or more carbon atoms.

m9 in Formula (f1) is preferably 1 or 2 and more preferably 1.

$X^9$ and $X^{10}$ in Formula (f1) are each independently preferably —O—, —S—, —COO—, —OCONH—, or —CONH—, and more preferably —O—.

$R^9$'s in Formula (f1) are each independently preferably an alkylene group having 1 to 10 carbon atoms, more preferably an alkylene group having 1 to 4 carbon atoms, and particularly preferably a methylene group.

$R^{10}$'s in Formula (f1) are each independently preferably a monovalent aliphatic hydrocarbon group having 5 to 60 carbon atoms, more preferably a monovalent aliphatic hydrocarbon group having 12 to 50 carbon atoms, still more preferably a monovalent aliphatic hydrocarbon group having 18 to 40 carbon atoms, and particularly preferably a monovalent aliphatic hydrocarbon group having 20 to 32 carbon atoms. In addition, $R^{10}$'s are each independently preferably a linear alkyl group or a branched alkyl group and more preferably a linear alkyl group.

m10 in Formula (f1) is preferably 2 or 3 and more preferably 2.

$Ar^1$ in Formula (f1) is preferably an (m10+1)-valent aromatic group, more preferably a group obtained by removing (m10+1) pieces of hydrogen atoms from benzene or a group obtained by removing (m10+1) pieces of hydrogen atoms from naphthalene, and particularly preferably a group obtained by removing (m10+1) pieces of hydrogen atoms from benzene.

In addition, from the viewpoint of deprotection rate and temporal stability, the group represented by Formula (f1) is preferably a group represented by Formula (f2).

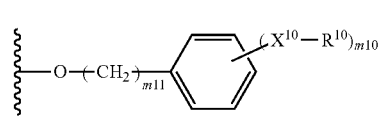
(f2)

In Formula (f2), a wavy line portion represents a bonding position to other configurations, m10 represents an integer of 1 to 3, m11 represents an integer of 1 to 3, $X^{10}$'s each independently represent a single bond, —O—, —S—, —COO—, —OCO—, —OCONH—, —NHCONH—, —NHCO—, or —CONH—, and $R^{10}$'s each independently represent a monovalent aliphatic hydrocarbon group having 5 or more carbon atoms.

m10, $X^{10}$, and $R^{10}$ in Formula (f2) have the same meaning as m10, $X^{10}$, and $R^{10}$ in Formula (f1), respectively, and the preferred aspects thereof are also the same.

m11 in Formula (f2) is preferably 1 or 2 and more preferably 1.

m20 in Formula (a1) is preferably 1 or 2 and more preferably 1.

$X^{20}$'s in Formula (a1) are each independently preferably —O—, —S—, —COO—, —OCONH—, or —CONH—, and more preferably —O—.

$R^{20}$ in Formula (a1) is preferably a divalent aliphatic hydrocarbon group having 5 or more carbon atoms, more preferably a divalent aliphatic hydrocarbon group having 5 to 60 carbon atoms, still more preferably a divalent aliphatic hydrocarbon group having 8 to 40 carbon atoms, and particularly preferably a divalent aliphatic hydrocarbon group having 12 to 32 carbon atoms. In addition, $R^{20}$ is preferably a linear alkylene group.

mb in Formula (b1) is preferably 1.

b1 to b4 in Formula (b1) are each independently preferably 1 or 2 and more preferably 1.

$X^{b1}$ to $X^{b4}$ in Formula (b1) are each independently preferably —O—, —S—, —COO—, —OCONH—, or —CONH—, and more preferably —O—.

$R^{b2}$ and $R^{b4}$ in Formula (b1) are each independently preferably a hydrogen atom, a methyl group, or an aliphatic hydrocarbon group having 5 to 60 carbon atoms, more preferably a hydrogen atom, a methyl group, or an alkyl group having 8 to 40 carbon atoms, and particularly preferably a hydrogen atom, a methyl group, or an alkyl group having 12 to 32 carbon atoms.

$R^{b3}$ in Formula (b1) is preferably a monovalent aliphatic hydrocarbon group having 5 to 60 carbon atoms, more preferably a monovalent aliphatic hydrocarbon group having 8 to 40 carbon atoms, and particularly preferably a monovalent aliphatic hydrocarbon group having 12 to 32 carbon atoms. In addition, $R^{63}$ is preferably a linear alkyl group.

From the viewpoint of deprotection rate and temporal stability, the compound represented by Formula (1) is preferably a compound represented by Formula (10).

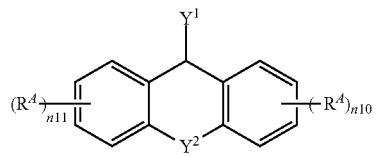

(10)

In Formula (10), $Y^1$ represents —$OR^{17}$, —$NHR^{18}$, —SH, or a halogen atom, where $R^{17}$ represents a hydrogen atom, an active ester-type carbonyl group, or an active ester-type sulfonyl group, and $R^{18}$ represents a hydrogen atom, a linear or branched alkyl group having 1 to 6 carbon atoms, an arylalkyl group, a heteroarylalkyl group, or an Fmoc group, $Y^2$ represents —$N(R^A)$—, —O—, —S—, —$CR^{100}$=$CR^{101}$—, —$CR^{102}R^{103}$—$CR^{104}R^{105}$—, or —$CR^{106}R^{107}$—, where $R^{100}$ to $R^{107}$ each independently represent a hydrogen atom or an alkyl group, $R^A$ represents an aliphatic hydrocarbon group or an organic group having an aliphatic hydrocarbon group, and the number of carbon atoms in at least one aliphatic hydrocarbon group of $R^A$ is 12 or more, where $R^A$ does not have a silyl group and a hydrocarbon group having a silyloxy structure, and n10 and n11 each independently represent an integer of 0 to 4, where both n10 and n11 cannot be 0.

$Y^1$ and $R^A$ in Formula (10) have the same meaning as $Y^1$ and $R^A$ in Formula (1), respectively, and the preferred aspects thereof are also the same.

n10 and n11 in Formula (10) are each independently preferably an integer of 0 to 2, and it is more preferable that any one of n10 or n11 is 0 and the other is 1.

From the viewpoint of deprotection rate and temporal stability, it is preferable that $R^A$ is bonded to any of a 2-position, a 3-position, a 4-position, a 5-position, a 6-position, or a 7-position of the condensed polycycle, it is more preferable to be bonded to any of a 2-position, a 3-position, a 6-position, or a 7-position of the condensed polycycle, and it is still more preferable to be bonded to any of a 3-position or a 6-position of the condensed polycycle.

From the viewpoint of deprotection rate and temporal stability, the compound represented by Formula (10) is preferably a compound represented by Formula (100) or Formula (200), and more preferably a compound represented by Formula (100).

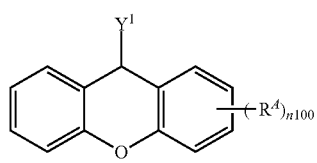

(100)

-continued

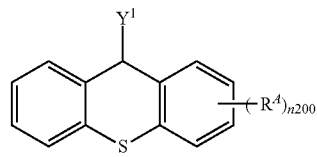

(200)

In Formula (100) or Formula (200), $Y^1$ represents —OH or —$NHR^{18}$, where $R^{18}$ represents a hydrogen atom, a linear or branched alkyl group having 1 to 6 carbon atoms, an arylalkyl group, a heteroarylalkyl group, or an Fmoc group, $R^A$ represents an aliphatic hydrocarbon group or an organic group having an aliphatic hydrocarbon group, and the number of carbon atoms in at least one aliphatic hydrocarbon group of $R^A$ is 12 or more, where $R^A$ does not have a silyl group and a hydrocarbon group having a silyloxy structure, and n100 and n200 each independently represent an integer of 1 to 4.

$R^A$ in Formula (100) and Formula (200) has the same meaning as $R^A$ in Formula (1), and the preferred aspects thereof are also the same. $R^{18}$ of $Y^1$ in Formula (100) and Formula (200) has the same meaning as $R^{18}$ of $Y^1$ in Formula (1), and the preferred aspects thereof are also the same.

From the viewpoint of deprotection rate and temporal stability, it is preferable that $R^A$ is bonded to any of a 2-position, a 3-position, or a 4-position of the condensed polycycle, it is more preferable to be bonded to any of a 2-position or a 3-position of the condensed polycycle, and it is still more preferable to be bonded to a 3-position of the condensed polycycle.

n100 and n200 are preferably an integer or 1 to 3, preferably 1 or 2, and more preferably 1.

From the viewpoint of deprotection rate and temporal stability, it is preferable that $R^A$ in Formula (10), Formula (100), and Formula (200) is a group represented by any of Formula (f1), Formula (a1), Formula (b1), or Formula (e1) described above, it is more preferable to be a group represented by any of Formula (f1) or Formula (a1) described above, it is still more preferable to be a group represented by Formula (f1) described above, and it is particularly preferable to be a group represented by Formula (f2).

From the viewpoint of deprotection rate and temporal stability, $R^{18}$ of $Y^1$ in Formula (10), Formula (100), and Formula (200) is preferably a hydrogen atom, an alkyl group having 1 to 6 carbon atoms, an arylalkyl group having 7 to 16 carbon atoms, or an Fmoc group, more preferably a hydrogen atom, a methyl group, an ethyl group, a benzyl group, or a Fmoc group, and still more preferably a hydrogen atom or an Fmoc group.

In a case where the compound represented by Formula (1) is the compound represented by Formula (100), from the viewpoint of deprotection rate and temporal stability, it is preferable that $R^A$ is bonded to the 3-position of the condensed polycycle, $Y^1$ represents —$NHR^{18}$ (preferably, a hydrogen atom, an alkyl group having 1 to 6 carbon atoms, an arylalkyl group having 7 to 16 carbon atoms, or an Fmoc group, more preferably a hydrogen atom, a methyl group, an ethyl group, a benzyl group, or an Fmoc group, and still more preferably a hydrogen atom or an Fmoc group), and $R^A$ is Formula (f1) (preferably, the group represented by Formula (f2)).

m9, $X^9$, $X^{10}$, $R^9$, $R^{10}$, m10, and $Ar^1$ in Formula (f1) have the same meaning as m9, $X^9$, $X^{10}$, $R^9$, $R^{10}$, m10, and $Ar^1$ in Formula (f1) described above, respectively, and the preferred aspects thereof are also the same. In addition, m10, $X^{10}$, and $R^{10}$ in Formula (f2) have the same meaning as m10, $X^{10}$, and $R^{10}$ in Formula (f1), respectively, and the preferred aspects thereof are also the same.

The molecular weight of the compound represented by Formula (1) is not particularly limited, but from the viewpoint of deprotection rate, crystallization property, solubility in a solvent, and yield, it is preferably 340 to 3,000, more preferably 400 to 2,000, still more preferably 500 to 1,500, and particularly preferably 800 to 1,300. In addition, in a case where the molecular weight is 3,000 or less, the proportion of Formula (1) in the target product is appropriate and the proportion of a compound obtained by deprotecting Formula (1) is not reduced, so that productivity is excellent.

Preferred specific examples of the compound represented by Formula (1) include compounds shown below, but needless to say, the compound represented by Formula (1) is not limited thereto. Me represents a methyl group, and Et represents an ethyl group.

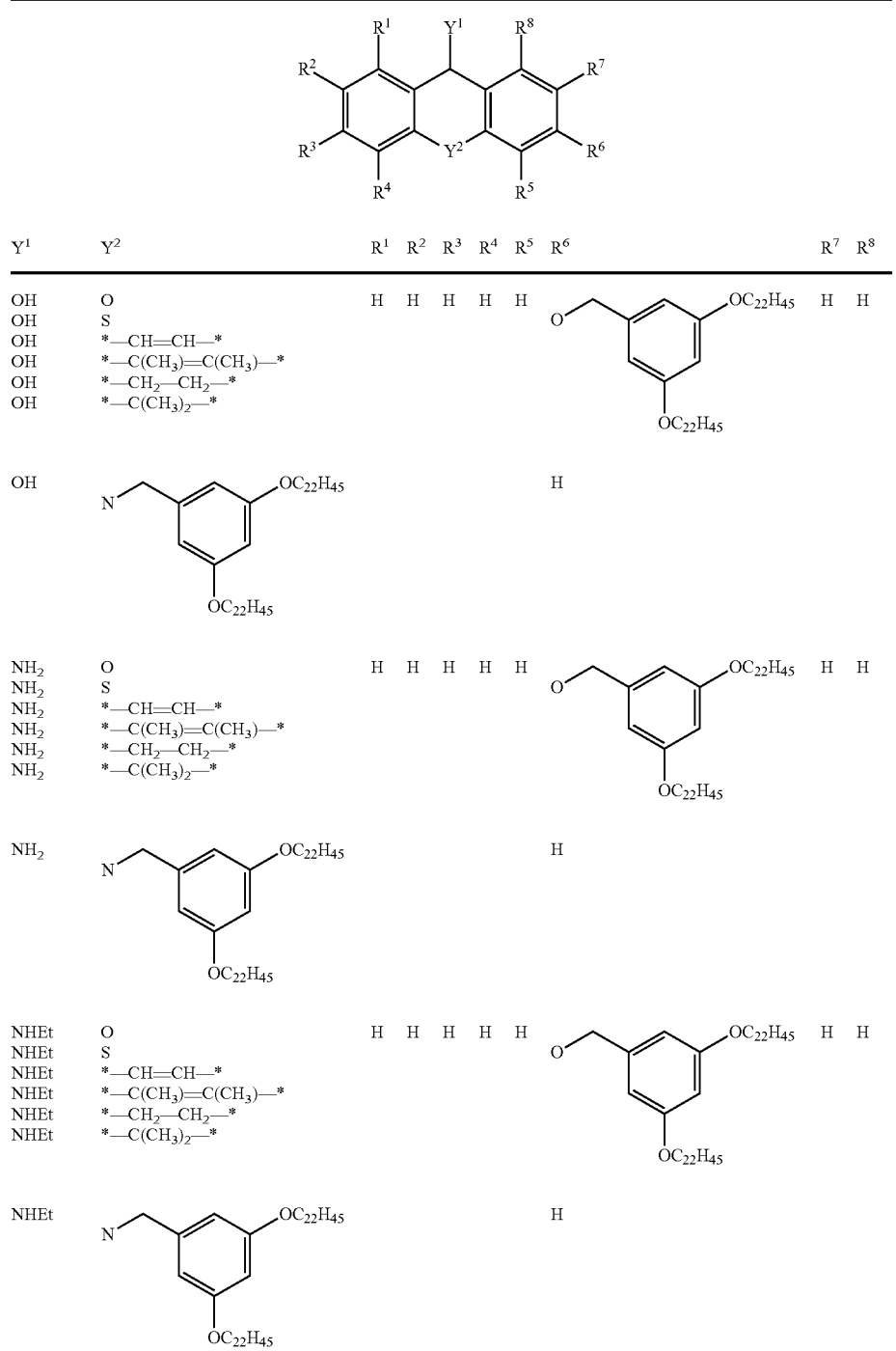

-continued

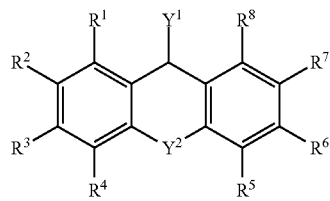

| Y¹ | Y² | R¹ | R² | R³ | R⁴ | R⁵ | R⁶ | R⁷ | R⁸ |
|---|---|---|---|---|---|---|---|---|---|
| NHFmoc | O | H | H | H | H | H | ![benzyl ether with OC₂₂H₄₅ groups] | H | H |
| NHFmoc | S | | | | | | | | |
| NHFmoc | *—CH=CH—* | | | | | | | | |
| NHFmoc | *—C(CH₃)=C(CH₃)—* | | | | | | | | |
| NHFmoc | *—CH₂—CH₂—* | | | | | | | | |
| NHFmoc | *—C(CH₃)₂—* | | | | | | | | |
| NHFmoc | [N-benzyl with two OC₂₂H₄₅ groups] | | | | | | H | | |

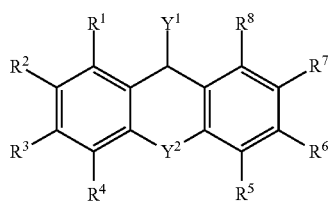

| Y¹ | Y² | R¹ | R² | R³ | R⁴ | R⁵ | R⁶ | R⁷ | R⁸ |
|---|---|---|---|---|---|---|---|---|---|
| SH | O | H | H | H | H | H | ![benzyl ether with OC₂₂H₄₅ groups] | H | H |
| SH | S | | | | | | | | |
| SH | *—CH=CH—* | | | | | | | | |
| SH | *—C(CH₃)=C(CH₃)—* | | | | | | | | |
| SH | *—CH₂—CH₂—* | | | | | | | | |
| SH | *—C(CH₃)₂—* | | | | | | | | |
| SH | [N-benzyl with two OC₂₂H₄₅ groups] | | | | | | H | | |
| Br | O | H | H | H | H | H | ![benzyl ether with OC₂₂H₄₅ groups] | H | H |
| Br | S | | | | | | | | |
| Br | *—CH=CH—* | | | | | | | | |
| Br | *—C(CH₃)=C(CH₃)—* | | | | | | | | |
| Br | *—CH₂—CH₂—* | | | | | | | | |
| Br | *—C(CH₃)₂—* | | | | | | | | |
| Br | [N-benzyl with two OC₂₂H₄₅ groups] | | | | | | H | | |

-continued

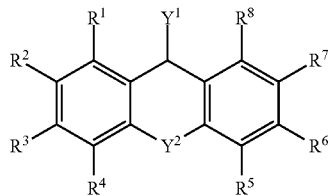

| Y¹ | Y² | R¹ | R² | R³ | R⁴ | R⁵ | R⁶ | R⁷ | R⁸ |
|---|---|---|---|---|---|---|---|---|---|
| Cl | O | H | H | H | H | H | 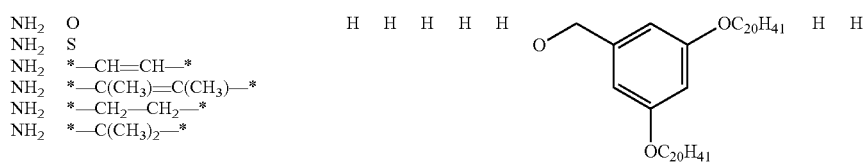 | H | H |
| Cl | S | | | | | | | | |
| Cl | *—CH=CH—* | | | | | | | | |
| Cl | *—C(CH₃)=C(CH₃)—* | | | | | | | | |
| Cl | *—CH₂—CH₂—* | | | | | | | | |
| Cl | *—C(CH₃)₂—* | | | | | | | | |
| Cl | 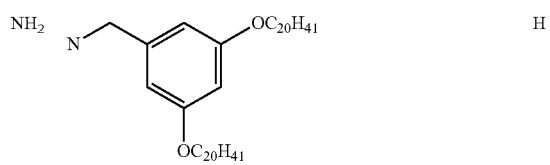 | | | | | | | | H |

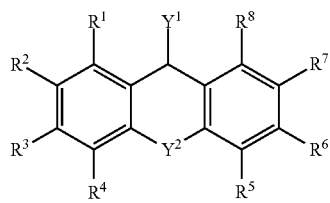

| Y¹ | Y² | R¹ | R² | R³ | R⁴ | R⁵ | R⁶ | R⁷ | R⁸ |
|---|---|---|---|---|---|---|---|---|---|
| NH₂ | O | H | H | H | H | H | (3,5-bis(OC₁₈H₃₇)benzyloxymethyl) | H | H |
| NH₂ | S | | | | | | | | |
| NH₂ | *—CH=CH—* | | | | | | | | |
| NH₂ | *—C(CH₃)=C(CH₃)—* | | | | | | | | |
| NH₂ | *—CH₂—CH₂—* | | | | | | | | |
| NH₂ | *—C(CH₃)₂—* | | | | | | | | |
| NH₂ | (3,5-bis(OC₁₈H₃₇)benzylamino) | | | | | | | | H |
| NH₂ | O | H | H | H | H | H | (3,5-bis(OC₂₀H₄₁)benzyloxymethyl) | H | H |
| NH₂ | S | | | | | | | | |
| NH₂ | *—CH=CH—* | | | | | | | | |
| NH₂ | *—C(CH₃)=C(CH₃)—* | | | | | | | | |
| NH₂ | *—CH₂—CH₂—* | | | | | | | | |
| NH₂ | *—C(CH₃)₂—* | | | | | | | | |
| NH₂ | (3,5-bis(OC₂₀H₄₁)benzylamino) | | | | | | | | H |

-continued

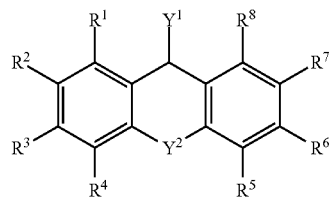

| Y¹ | Y² | R¹ | R² | R³ | R⁴ | R⁵ | R⁶ | R⁷ | R⁸ |
|---|---|---|---|---|---|---|---|---|---|
| $NH_2$ | O | H | H | H | H | H | ![benzyloxy-tri-OC18H37] | H | H |
| $NH_2$ | S | | | | | | | | |
| $NH_2$ | *—CH=CH—* | | | | | | | | |
| $NH_2$ | *—C(CH₃)=C(CH₃)—* | | | | | | | | |
| $NH_2$ | *—CH₂—CH₂—* | | | | | | | | |
| $NH_2$ | *—C(CH₃)₂—* | | | | | | | | |
| $NH_2$ | ![N-benzyl-tri-OC18H37] | | | | | | H | | |

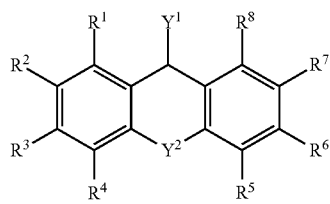

| Y¹ | Y² | R¹ | R² | R³ | R⁴ | R⁵ | R⁶ | R⁷ | R⁸ |
|---|---|---|---|---|---|---|---|---|---|
| $NH_2$ | O | H | H | ![benzyloxy-3,5-di-OC22H45] | $NH_2$ | H | ![benzyloxy-3,5-di-OC22H45] | H | H |
| $NH_2$ | S | | | | | | | | |
| $NH_2$ | *—CH=CH—* | | | | | | | | |
| $NH_2$ | *—C(CH₃)=C(CH₃)—* | | | | | | | | |
| $NH_2$ | *—CH₂—CH₂—* | | | | | | | | |
| $NH_2$ | *—C(CH₃)₂—* | | | | | | | | |
| $NH_2$ | O | H | H | H | H | H | $OC_{22}H_{45}$ | H | H |
| $NH_2$ | S | | | | | | | | |
| $NH_2$ | *—CH=CH—* | | | | | | | | |
| $NH_2$ | *—C(CH₃)=C(CH₃)—* | | | | | | | | |
| $NH_2$ | *—CH₂—CH₂—* | | | | | | | | |
| $NH_2$ | *—C(CH₃)₂—* | | | | | | | | |
| $NH_2$ | O | H | H | $OC_{22}H_{45}$ | H | H | $OC_{22}H_{45}$ | H | H |
| $NH_2$ | S | | | | | | | | |
| $NH_2$ | *—CH=CH—* | | | | | | | | |
| $NH_2$ | *—C(CH₃)=C(CH₃)—* | | | | | | | | |
| $NH_2$ | *—CH₂—CH₂—* | | | | | | | | |
| $NH_2$ | *—C(CH₃)₂—* | | | | | | | | |
| $NH_2$ | O | H | H | $OC_{12}H_{24}OC_{22}H_{45}$ | H | H | $OC_{12}H_{24}OC_{22}H_{45}$ | H | H |
| $NH_2$ | S | | | | | | | | |
| $NH_2$ | *—CH=CH—* | | | | | | | | |
| $NH_2$ | *—C(CH₃)=C(CH₃)—* | | | | | | | | |
| $NH_2$ | *—CH₂—CH₂—* | | | | | | | | |
| $NH_2$ | *—C(CH₃)₂—* | | | | | | | | |

<Method for Producing Compound Represented by Formula (1)>

A method for producing the compound represented by Formula (1) according to the present disclosure is not particularly limited, and can be produced by referring to a known method.

Unless otherwise specified, a raw material compound used for producing the compound represented by Formula (1) may be a commercially available compound, or may be produced by a known method or a method according to the known method.

In addition, the produced compound represented by Formula (1) may be purified by a known purification method as necessary. For example, a method of isolating and purifying by recrystallization, column chromatography, or the like, a method of purifying by reprecipitation with a unit for changing the solution temperature, a unit for changing the solution composition, or the like, and the like can be performed.

The method for synthesizing the compound represented by Formula (1) according to the present disclosure is not particularly limited, but the compound represented by Formula (1) can be synthesized according to, for example, the following scheme using 3-hydroxyxanthone and the like as a starting material. In addition, it is also possible to synthesize by referring to the synthesis method described in WO2018/021233A.

(Method for Producing Peptide Compound)

In the method for producing a peptide compound according to the embodiment of the present disclosure, it is preferable that the step of using the compound represented by Formula (1) is a C-terminal protecting step of protecting a carboxy group or an amide group of an amino acid compound or a peptide compound with the compound represented by Formula (1).

In addition, from the viewpoint of ease of synthesizing the peptide compound and yield, it is more preferable that the method for producing a peptide compound according to the embodiment of the present disclosure further includes, in addition to the above-described C-terminal protecting step of protecting a carboxy group or an amide group of an amino acid compound or a peptide compound with the compound represented by Formula (1), an N-terminal deprotecting step of deprotecting an N-terminal end of an N-terminal and C-terminal protected amino acid compound or an N-terminal and C-terminal protected peptide compound, which is obtained in the C-terminal protecting step, and a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound; it is still more preferable that the method for producing a peptide compound according to the embodiment of

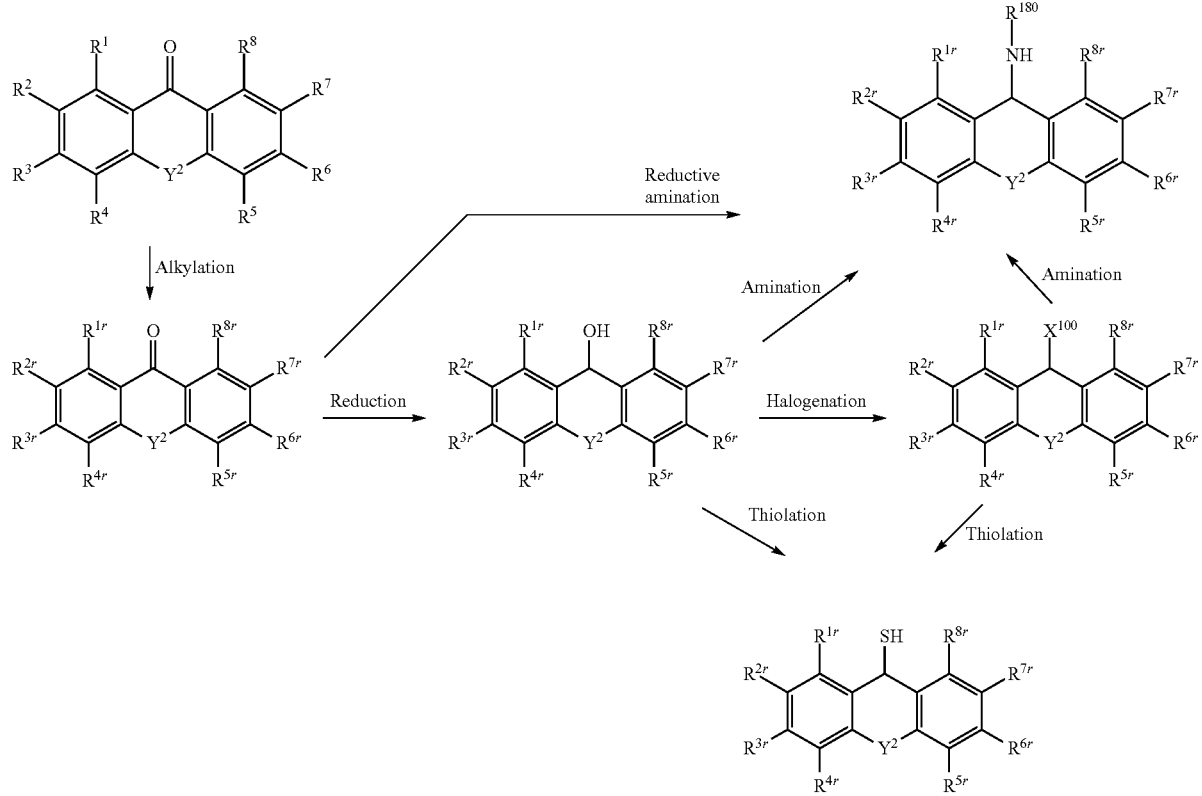

$R^{1r}$ to $R^{8r}$ each independently represent $R^A$, a hydrogen atom, a halogen atom, an alkyl group having 1 to 4 carbon atoms, or an alkoxy group having 1 to 4 carbon atoms, where at least one of $R^{1r}$ to $R^{8r}$ or $Y^2$ represents $R^A$. $X^{100}$ represents Cl, Br, or I. $R^{180}$ represents a hydrogen atom, an alkyl group, or an Fmoc group.

the present disclosure further includes, in addition to the above steps, a precipitating step of precipitating an N-terminal and C-terminal protected peptide compound obtained in the peptide chain extending step; and it is particularly preferable that the method for producing a peptide compound according to the embodiment of the present disclosure further includes, one or more times in the following order after the precipitating step, a step of deprotecting the N-terminal end of the obtained N-terminal and C-terminal protected peptide compound, a step of condensing the N-terminal end of the obtained C-terminal protected peptide compound with an N-terminal protected amino acid compound or an N-terminal protected peptide compound, and a step of precipitating the obtained N-terminal and C-terminal protected peptide compound.

In addition, it is preferable that the method for producing a peptide compound according to the embodiment of the present disclosure further includes a C-terminal deprotecting step of deprotecting a C-terminal protective group.

Furthermore, it is preferable that the method for producing a peptide compound according to the embodiment of the present disclosure further includes, before the above-described C-terminal protecting step, a dissolving step of dissolving the compound represented by Formula (1) in a solvent.

Hereinafter, each step and the like described above will be described in detail.

<Dissolving Step>

It is preferable that the method for producing a peptide compound according to the embodiment of the present disclosure includes, before the above-described C-terminal protecting step, a dissolving step of dissolving the compound represented by Formula (1) in a solvent.

As the solvent, a general organic solvent can be used for the reaction, but since excellent reactivity can be expected as solubility in the above-described solvent is higher, it is preferable to select a solvent having a high solubility of the condensed polycyclic aromatic hydrocarbon compound represented by Formula (1). Specific examples thereof include halogenated hydrocarbons such as chloroform and dichloromethane; and nonpolar organic solvents such as 1,4-dioxane, tetrahydrofuran, and cyclopentyl methyl ether. Two or more of these solvents may be mixed and used in an appropriate ratio. In addition, as long as the compound represented by Formula (1) can be dissolved, in the above-described halogenated hydrocarbons or nonpolar organic solvents, aromatic hydrocarbons such as benzene, toluene, and xylene; nitriles such as acetonitrile and propionitrile; ketones such as acetone and 2-butanone; amides such as N,N-dimethylformamide and N-methylpyrrolidone; and sulfoxides such as dimethyl sulfoxide may be mixed and used in an appropriate ratio.

In addition, a solvent described in Organic Process Research & Development, 2017, 21, 3, 365 to 369 may be used.

<C-Terminal Protecting Step>

It is preferable that the method for producing a peptide compound according to the embodiment of the present disclosure includes a C-terminal protecting step of protecting a carboxy group or an amide group of an amino acid compound or a peptide compound with the compound represented by Formula (1).

The amino acid compound or peptide compound used in the above-described C-terminal protecting step is not particularly limited, and a known compound can be used. However, an N-terminal protected amino acid compound or an N-terminal protected peptide compound is preferable, and an Fmoc-protected amino acid compound or an Fmoc-protected peptide compound is more preferable.

In addition, it is preferable that a hydroxy group, an amino group, a carbonyl group, an amide group, an imidazole group, an indole group, a guanidyl group, a mercapto group, or the like, which is a moiety other than the C-terminal end in the amino acid compound or peptide compound used in the above-described C-terminal protecting step, is protected by a known protective group such as a protective group described later.

The amount of the amino acid compound or peptide compound, which is used as a reaction substrate, to be used is preferably 1 molar equivalent to 10 molar equivalent, more preferably 1 molar equivalent to 5 molar equivalent, still more preferably 1 molar equivalent to 2 molar equivalent, and particularly preferably 1 molar equivalent to 1.5 molar equivalent with respect to 1 molar equivalent of the compound represented by Formula (1).

In a case where a compound represented by Formula (1), in which $Y^1$ in Formula (1) is —OH, is used, it is preferable to add a condensing agent in the presence of a condensation additive (condensation activating agent) in a solvent which does not affect the reaction, or to react in an acid catalyst.

In a case where a compound represented by Formula (1), in which $Y^1$ in Formula (1) is —$NHR^{18}$, is used, it is preferable to add a condensing agent in the presence of a condensation additive (condensation activating agent), or to react with a condensing agent and a base.

The amount of the condensation additive to be used is preferably 0.05 molar equivalent to 1.5 molar equivalent with respect to 1 molar equivalent of the condensed polycyclic aromatic hydrocarbon compound represented by Formula (1).

As the condensing agent, a condensing agent generally used in peptide synthesis can be used without limitation in the present disclosure. Examples thereof include 4-(4,6-dimethoxy-1,3,5-triazin-2-yl)-4-methylmorpholinium chloride (DMT-MM), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), O-(6-chlorobenzotriazol-1-yl)-1,1,3,3-tetramethyluronium hexafluorophosphate (HBTU(6-Cl)), O-(benzotriazol-1-yl)-1,1,3,3-tetramethyluronium tetrafluoroborate (TBTU), O-(6-chlorobenzotriazol-1-yl)-1,1,3,3-tetramethyluronium tetrafluoroborate (TCTU), (1-cyano-2-ethoxy-2-oxoethylidenaminooxy)dimethylamino-morpholino-carbenium hexafluorophosphate (COMU), dicyclohexylcarbodiimide (DCC), diisopropylcarbodiimide (DIC), 1-ethyl-3-(3-dimethylaminopropyl) carbodiimide (EDC), a hydrochloride salt (EDC/HCl) of 1-ethyl-3-(3-dimethylaminopropyl) carbodiimide, and (benzotriazol-1-yloxy)tripyrrolidinophosphonium hexafluorophosphate (PyBoP), but the condensing agent is not limited thereto.

Among these, DIC, EDC, EDC/HCl, DMT-MM, HBTU, HATU, or COMU is preferable.

The amount of the condensing agent to be used is preferably 1 molar equivalent to 10 molar equivalent and more preferably 1 molar equivalent to 5 molar equivalent with respect to 1 molar equivalent of the compound represented by Formula (1).

As the acid catalyst used in the condensation reaction, an acid catalyst generally used in peptide synthesis can be used without limitation, and examples thereof include methanesulfonic acid, trifluoromethanesulfonic acid, and p-toluenesulfonic acid.

Among these, methanesulfonic acid or p-toluenesulfonic acid is preferable.

The amount of the acid catalyst to be used is preferably more than 0 molar equivalent and 4.0 molar equivalent or less, more preferably 0.05 molar equivalent to 1.5 molar equivalent, and still more preferably 0.1 molar equivalent to 0.3 molar equivalent with respect to 1 molar equivalent of the compound represented by Formula (1).

In the above-described C-terminal protecting step, it is preferable to add an activating agent in order to promote the reaction and suppress side reactions such as racemization.

The activating agent in the present disclosure is a reagent which, in a case of coexisting with the condensing agent, leads an amino acid to a corresponding active ester, symmetric acid anhydride, or the like to facilitate the formation of a peptide bond (amide bond).

As the activating agent, an activating agent generally used in peptide synthesis can be used without limitation, and examples thereof include 4-dimethylaminopyridine, N-methylimidazole, boronic acid derivative, 1-hydroxybenzotriazole (HOBt), ethyl 1-hydroxytriazole-4-carboxylate (HOCt), 1-hydroxy-7-azabenzotriazole (HOAt), 3-hydroxy-1,2,3-benzotriazin-4(3H)-one (HOOBt), N-hydroxysuccinimide (HOSu), N-hydroxyphthalimide (HOPht), N-hydroxy-5-norbornene-2,3-dicarboxyimide (HONb), pentafluorophenol, and ethyl(hydroxyimino)cyanoacetylate (Oxyma). Among these, 4-dimethylaminopyridine, HOBt, HOCt, HOAt, HOOBt, HOSu, HONb, or Oxyma is preferable.

The amount of the activating agent to be used is preferably more than 0 molar equivalent and 4.0 molar equivalent or less and more preferably 0.1 molar equivalent to 1.5 molar equivalent with respect to the amino acid compound or peptide compound.

As the base, a base generally used in peptide synthesis can be used without limitation, and examples thereof include a tertiary amine such as diisopropylethylamine.

As the solvent, the above-described solvent used in the above-described dissolving step can be suitably used.

The reaction temperature is not particularly limited, but is preferably −10° C. to 80° C. and more preferably 0° C. to 40° C. The reaction time is not particularly limited, but is preferably 1 hour to 30 hours.

To confirm the progress of the reaction, a method same as that of a general liquid phase organic synthesis reaction can be applied. That is, the reaction can be traced using thin-layer silica gel chromatography, high performance liquid chromatography, NMR, or the like.

In addition, the N-terminal and C-terminal protected amino acid compound or N-terminal and C-terminal protected peptide compound obtained by the above-described C-terminal protecting step may be purified.

For example, in order to isolate the product obtained after dissolving the obtained N-terminal and C-terminal protected amino acid compound or N-terminal and C-terminal protected peptide compound in a solvent (reaction solvent) and performing a desired organic synthesis reaction. It is preferable to perform a method of changing the solvent to a solvent in which the N-terminal and C-terminal protected amino acid compound or N-terminal and C-terminal protected peptide compound is dissolved (for example, change of solvent composition or change of solvent type) and reprecipitating the resultant.

Specifically, the reaction is performed under conditions such that the N-terminal and C-terminal protected amino acid compound or N-terminal and C-terminal protected peptide compound is dissolved. After the reaction, the solvent is distilled off and then replaced, or after the reaction, by adding a polar solvent to the reaction system without distilling off the solvent, aggregates are precipitated and impurities are eliminated.

As the solvent for replacement or the polar solvent, polar organic solvents such as methanol, acetonitrile, and water are used alone or in combination. That is, the reaction is performed under conditions such that the N-terminal and C-terminal protected amino acid compound or N-terminal and C-terminal protected peptide compound is dissolved, and in the solvent replacement after the reaction, for example, a halogenated solvent, THF, or the like is used for dissolution, and a polar organic solvent such as methanol, acetonitrile, and water is used for precipitation.

<N-Terminal Deprotecting Step>

It is preferable that the method for producing a peptide compound according to the embodiment of the present disclosure includes an N-terminal deprotecting step of deprotecting an N-terminal end of the N-terminal and C-terminal protected amino acid compound or N-terminal and C-terminal protected peptide compound, which is obtained in the C-terminal protecting step.

As the N-terminal protective group, a protective group for an amino group described later, which is generally used in technical fields such as peptide chemistry, can be used, but in the present disclosure, a Boc group, a benzyloxycarbonyl group (hereinafter, also referred to as a Cbz group or a Z group), or an Fmoc group is suitably used.

The deprotection condition is appropriately selected depending on the type of the temporary protective group, but a group which can be deprotected under conditions different from the removal of the protective group derived from the compound represented by Formula (1) is preferable. For example, in a case of the Fmoc group, the deprotection is performed by treating with a base, and in a case of the Boc group, the deprotection is performed by treating with an acid. The reaction is performed in a solvent which does not affect the reaction.

Examples of the base include secondary amines such as dimethylamine and diethylamine, and non-nucleophilic organic bases such as 1,8-diazabicyclo[5.4.0]-7-undecene (DBU), 1,4-diazabicyclo[2.2.2]octane (DABCO), and 1,5-diazabicyclo[4.3.0]-5-nonene (DBN).

As the solvent, the above-described solvent used in the above-described dissolving step can be suitably used.

<Peptide Chain Extending Step>

It is preferable that the method for producing a peptide compound according to the embodiment of the present disclosure includes a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound.

The above-described peptide chain extending step is preferably performed under peptide synthesis conditions generally used in the field of peptide chemistry, in which the above-described condensing agent, condensation additive, and the like are used.

The N-terminal protected amino acid compound or N-terminal protected peptide compound is not particularly limited, and a desired compound can be used. However, an Fmoc-protected amino acid compound or an Fmoc-protected peptide compound can be suitably used.

In addition, it is preferable that a hydroxy group, an amino group, a carbonyl group, an amide group, an imidazole group, an indole group, a guanidyl group, a mercapto group, or the like, which is a moiety other than the C-terminal end in the N-terminal protected amino acid compound or N-terminal protected peptide compound, is protected by a known protective group such as a protective group described later.

<Precipitating Step>

It is preferable that the method for producing a peptide compound according to the embodiment of the present disclosure further includes a precipitating step of precipitating the N-terminal and C-terminal protected peptide compound obtained in the peptide chain extending step.

The precipitating step can be performed in the same manner as in the purification (reprecipitation) of the C-terminal protecting step described above.

Specifically, a polar solvent is added to the reaction system without distilling off the reaction solvent after the reaction in the previous stage. In this case, in the reaction solvent, THF is used as the nonpolar organic solvent and acetonitrile is used as the polar solvent. The proportion (volume basis) of the nonpolar organic solvent and the polar solvent used is preferably 1:1 to 1:100, more preferably 1:3 to 1:50, and still more preferably 1:5 to 1:20. In the case of this proportion used, the N-terminal and C-terminal protected amino acid compound or N-terminal and C-terminal protected peptide compound can be efficiently precipitated, and the target product can be efficiently purified.

<Chain Extension>

It is preferable that the method for producing a peptide compound according to the embodiment of the present disclosure further includes, one or more times in the following order after the precipitating step, a step of deprotecting an N-terminal end of the obtained N-terminal and C-terminal protected peptide compound, a step of condensing the N-terminal end of the obtained C-terminal protected peptide compound with an N-terminal protected amino acid compound or an N-terminal protected peptide compound, and a step of precipitating the obtained N-terminal and C-terminal protected peptide compound.

By repeating the above-described three steps, the chain extension of the obtained peptide compound can be easily performed.

Each step in the above-described three steps can be performed in the same manner as each corresponding step described above.

<C-Terminal Deprotecting Step>

It is preferable that the method for producing a peptide compound according to the embodiment of the present disclosure further includes a C-terminal deprotecting step of deprotecting a C-terminal protective group.

In the above-described C-terminal deprotecting step, by removing the C-terminal protective group formed by the compound represented by Formula (1) in the C-terminal protected peptide compound having a desired number of amino acid residues, a peptide compound, which is the final target product, can be obtained.

Preferred examples of a method of removing the C-terminal protective group include a deprotecting method using an acidic compound.

Examples thereof include a method of adding an acid catalyst and a hydrogenating method using a metal catalyst. Examples of the acid catalyst include trifluoroacetic acid (TFA), hydrochloric acid, trifluoroethanol (TFE), hexafluoroisopropanol (HFIP), and acetic acid, and TFA is preferable for peptides which do not decompose with strong acids, and TFE, HFIP, or acetic acid is preferable for peptides which decompose with strong acids. The concentration of the acid can be appropriately selected depending on the side chain protective group of the extending amino acid and the deprotection conditions, and examples thereof include 0.01% by mass to 100% by mass with respect to the total mass of the solvent used.

The concentration of TFA is preferably 70% by mass or less, more preferably 50% by mass or less, still more preferably 30% by mass or less, and particularly preferably 10% by mass or less.

The concentration of TFA is preferably 10% by volume or less, more preferably 5% by volume or less, and particularly preferably 1% by volume or less with respect to the total volume of the solvent used. The lower limit value is preferably 0.01% by volume, more preferably 0.1% by volume, and still more preferably 0.5% by volume.

The deprotection time is preferably 5 hours or less, more preferably 3 hours or less, and still more preferably 1 hour or less.

In the present disclosure, the C-terminal protective group can be deprotected even under weak acid conditions, and a side reaction of the obtained peptide can be suppressed.

Examples of peptide which is suitable for deprotection of the C-terminal protective group under weak acid conditions (that is, peptide which is sensitive to acid) include peptides having an N-alkylamide structure.

From the viewpoint of suppressing side reactions of the obtained peptide and of temporal stability, the method for producing a peptide compound according to the embodiment of the present disclosure is preferably used for a method for producing a peptide compound which is sensitive to acid, more preferably used for a method for producing a peptide compound having an N-alkylamide structure.

The peptide compound, which is the final target product obtained by the method for producing a peptide compound according to the embodiment of the present disclosure, can be isolated and purified according to a method commonly used in peptide chemistry. For example, the peptide compound, which is the final target product, can be isolated and purified by extraction and washing the reaction mixture, crystallization, chromatography, and the like.

The type of peptide produced by the method for producing a peptide compound according to the embodiment of the present disclosure is not particularly limited, but it is preferable that the number of amino acid residues of the peptide compound is, for example, approximately several tens or less. Same as existing or unknown synthetic or native peptides, the peptide obtained by the method for producing a peptide compound according to the embodiment of the present disclosure can be used in various fields such as pharmaceuticals, foods, cosmetics, electronic materials, biosensors, and the like, but the use of the peptide is not limited thereto.

In the method for producing a peptide compound according to the embodiment of the present disclosure, the precipitating step can be appropriately omitted as long as it does not affect the reaction in the next step.

In a case where the amino acid compound or peptide compound used in the method for producing a peptide compound according to the embodiment of the present disclosure has a hydroxy group, an amino group, a carboxy group, a carbonyl group, a guanidyl group, a mercapto group, or the like, a protective group generally used in peptide chemistry or the like may be introduced into these groups, and the target compound can be obtained by removing the protective group as necessary after the reaction.

Examples of a protective group of the hydroxy group include an alkyl group having 1 to 6 carbon atoms, an aryl group, a trityl group, an aralkyl group having 7 to 10 carbon atoms, a formyl group, an acyl group having 1 to 6 carbon atoms, a benzoyl group, an aralkyl-carbonyl group having 7 to 10 carbon atoms, a 2-tetrahydropyranyl group, a 2-tetrahydrofuranyl group, a silyl group, and an alkenyl group having 2 to 6 carbon atoms. These groups may be substituted with one to three substituents selected from the group consisting of a halogen atom, an alkyl group having 1 to 6 carbon atoms, and a nitro group.

Examples of a protective group of the amino group include a formyl group, an acyl group having 1 to 6 carbon atoms, an alkoxycarbonyl group having 1 to 6 carbon atoms, a benzoyl group, an aralkyl-carbonyl group having 7 to 10 carbon atoms, an aralkyloxycarbonyl group having 7 to 14 carbon atoms, a trityl group, a monomethoxytrityl group, a 1-(4,4-Dimethyl-2,6-dioxocyclohex-1-ylidene)-3-methylbutyl group, a phtaloyl group, an N,N-dimethylaminomethylene group, a silyl group, and an alkenyl group having 2 to 6 carbon atoms. These groups may be substituted with one to three substituents selected from the group consisting of a halogen atom, an alkoxy group having 1 to 6 carbon atoms, and a nitro group.

Examples of a protective group of the carboxy group include the above-described protective group of the hydroxy group and a trityl group.

Examples of a protective group of the carbonyl group include cyclic acetals (for example, 1,3-dioxane) and acyclic acetals (for example, di(alkyl having 1 to 6 carbon atoms) acetal).

Examples of a protective group of the guanidyl group include a 2,2,4,6,7-pentamethyldihydrobenzofuran-5-sulfonyl group, a 2,3,4,5,6-pentamethylbenzenesulfonyl group, a tosyl group, and a nitro group.

Examples of a protective group of the mercapto group (sulfhydryl group) include a trityl group, a 4-methylbenzyl group, an acetylaminomethyl group, a t-butyl group, and a t-butylthio group.

The method of removing these protective groups may be performed according to a known method described in, for example, Protective Groups in Organic Synthesis, John Wiley and Sons (1980). For example, a method using acid, base, ultraviolet light, hydrazine, phenylhydrazine, sodium N-methyldithiocarbamate, tetrabutylammonium fluoride, palladium acetate, trialkylsilyl halide, or the like, a reduction method, and the like are used.

(Protective Group-Forming Reagent)

The protective group-forming reagent according to the embodiment of the present disclosure includes the above-described compound represented by Formula (1). According to another embodiment of the present invention, it is possible to provide a protective group-forming reagent having an excellent yield. In particular, it is possible to provide a protective group-forming reagent having an excellent deprotection rate and temporal stability.

The protective group-forming reagent according to the embodiment of the present disclosure is preferably a protective group-forming reagent of a carboxy group or an amide group, and more preferably a C-terminal protective group-forming reagent of an amino acid compound or a peptide compound.

A preferred aspect of the compound represented by Formula (1) in the protective group-forming reagent according to the embodiment of the present disclosure is the same as the above-described preferred aspect of the compound represented by Formula (1) according to the present disclosure.

The content of the condensed polycyclic aromatic hydrocarbon compound represented by Formula (1) in the protective group-forming reagent according to the embodiment of the present disclosure is not particularly limited, but is preferably 0.1% by mass to 100% by mass, more preferably 1% by mass to 100% by mass, and still more preferably 3% by mass to 100% by mass with respect to the total mass of the protective group-forming reagent.

The protective group-forming reagent according to the embodiment of the present disclosure may include a component other than the compound represented by Formula (1).

(Condensed Polycyclic Compound Represented by Formula (1a))

The compound according to the embodiment of the present disclosure is a condensed polycyclic compound represented by Formula (1a).

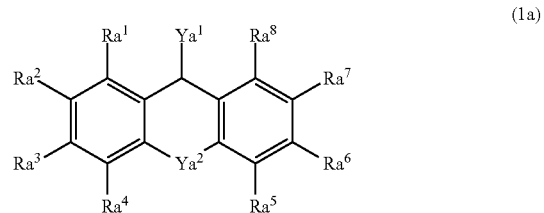

(1a)

In Formula (1a), $Ya^1$ represents —$ORa^{17}$, —$NHRa^{18}$, —SH, or a halogen atom, where $Ra^{17}$ represents a hydrogen atom, an active ester-type carbonyl group, or an active ester-type sulfonyl group, and $Ra^{18}$ represents a hydrogen atom, a linear or branched alkyl group having 10 or less carbon atoms, an arylalkyl group, a heteroarylalkyl group, or an Fmoc group, $Ya^2$ represents —$N(R^{110})$—, —O—, —S—, —$CRa^{100}$=$CRa^{101}$—, —$CRa^{102}Ra^{103}$—$CRa^{104}Ra^{105}$—, or —$CRa^{106}Ra^{107}$—, where $R^{110}$ represents $R^A$ or an alkyl group, and $Ra^{100}$ to $Ra^{107}$ each independently represent a hydrogen atom or an alkyl group, $Ra^1$ to $Ra^8$ each independently represent $R^A$, a hydrogen atom, a halogen atom, an alkyl group having 1 to 4 carbon atoms, or an alkoxy group having 1 to 4 carbon atoms, at least one of $Ra^2$, . . . , or $Ra^7$ has $R^A$ $R^A$ represents an aliphatic hydrocarbon group or an organic group having an aliphatic hydrocarbon group, and the number of carbon atoms in at least one aliphatic hydrocarbon group of $R^A$ is 12 or more, provided that, $R^A$ does not have a silyl group and a hydrocarbon group having a silyloxy structure.

The condensed polycyclic compound represented by Formula (1a), which is the compound according to the embodiment of the present disclosure, is a novel compound and can be suitably used for producing a peptide compound. Among these, the compound according to the embodiment of the present disclosure can be suitably used as a protective group-forming reagent, more suitably used as a protective group-forming reagent of a carboxy group or an amide group, and particularly suitably used as a C-terminal protective group-forming reagent of an amino acid compound or a peptide compound.

$Ra^{17}$ and $Ra^{18}$ in Formula (1a) have the same meaning as $R^{17}$ and $R^{18}$ in Formula (1), and the preferred aspects thereof are also the same.

$Ya^2$ in Formula (1a) has the same meaning as $Y^2$ in Formula (1), and the preferred aspects thereof are also the same.

$R^A$ in Formula (1a) has the same meaning as $R^A$ in Formula (1), and the preferred aspects thereof are also the same.

The condensed polycyclic compound represented by Formula (1a) in the compound according to the present disclosure is the same as the compound represented by Formula (1) in the above-described method for producing a peptide compound according to the embodiment of the present disclosure, except that at least one of $Ra^2, \ldots,$ or $Ra^7$ has $R^A$. In addition, the same applies to preferred aspects other than the preferred aspect described later.

The condensed polycyclic compound represented by Formula (1a) is a compound in which at least one of $Ra^2, \ldots,$ or $Ra^7$ has $R^A$, and from the viewpoint of deprotection rate and temporal stability, preferably a compound in which at least one of $Ra^3$ or $Ra^6$ has $R^A$, and more preferably a compound in which any one of $Ra^3$ or $Ra^6$ has $R^A$.

From the viewpoint of deprotection rate and temporal stability, the condensed polycyclic compound represented by Formula (1a) is preferably a compound represented by any of Formula (100a) or Formula (200a), and more preferably a compound represented by Formula (100a).

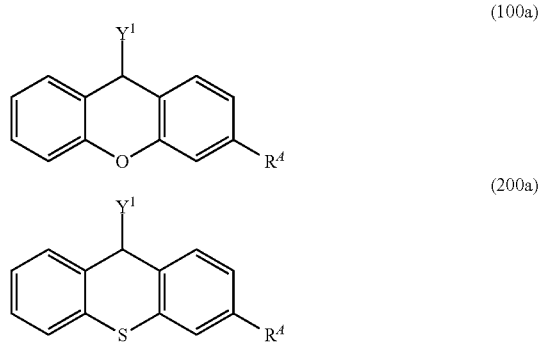

In Formula (100a) and Formula (200a), $Y^1$ represents —OH or —NH$_2$, $R^A$ represents an aliphatic hydrocarbon group or an organic group having an aliphatic hydrocarbon group, and the number of carbon atoms in at least one aliphatic hydrocarbon group of $R^A$ is 12 or more, provided that $R^A$ does not have a silyl group and a hydrocarbon group having a silyloxy structure.

$R^A$ in the compound represented by Formula (100a) and Formula (200a) has the same meaning as $R^A$ in the compound represented by Formula (1a), and the preferred aspects thereof are also the same.

In addition, the condensed polycyclic compound represented by Formula (1a) can be synthesized in the same manner as in the compound represented by Formula (1).

EXAMPLES

Hereinafter, the embodiments of the present invention will be more specifically described with reference to Examples. The materials, amounts to be used, proportions, treatment contents, treatment procedures, and the like shown in Examples can be appropriately modified as long as the modifications do not depart from the spirit of the embodiments of the present invention. Therefore, the scope of the embodiments of the present invention is not limited to the following specific examples. In addition, "parts" and "%" are on a mass basis unless otherwise specified. The room temperature means 25° C.

Unless otherwise specified, purification by column chromatography was performed using an automatic purification device ISOLERA (manufactured by Biotage Ltd.) or a medium pressure liquid chromatograph YFLC-Wprep 2XYN (manufactured by YAMAZEN).

Unless otherwise specified, SNAPKP-Sll Cartridge (manufactured by Biotage Ltd.) or a high flash column W001, W002, W003, W004, or W005 (manufactured by YAMAZEN) was used as a carrier in silica gel column chromatography.

The mixing ratio in an eluent used for column chromatography is the volume ratio. For example, "gradient elution of hexane:ethyl acetate=50:50 to 0:100" means that an eluent of 50% hexane and 50% ethyl acetate is finally changed to an eluent of 0% hexane and 100% ethyl acetate.

In addition, "gradient elution of hexane:ethyl acetate=50:50 to 0:100 and gradient elution of methanol:ethyl acetate=0:100 to 20:80" means that an eluent of 50% hexane and 50% ethyl acetate is changed to an eluent of 0% hexane and 100% ethyl acetate, and then the eluent of 0% hexane and 100% ethyl acetate is finally changed to an eluent of 20% methanol and 80% ethyl acetate.

MS spectrum was measured using ACQUITY SQD LC/MS System (manufactured by Waters Corporation; ionization method; electrospray ionization (ESI) method).

NMR spectrum was measured using Bruker AV300 (manufactured by Bruker, 300 MHz) or Bruker AV400 (manufactured by Bruker, 400 MHz), using tetramethylsilane as an internal reference, and all S values were represented in ppm.

The HPLC purity was measured using ACQUITY UPLC (manufactured by Waters Corporation, column: CSH C18 1.7 μm).

Synthesis of Protective Group-Forming Reagents (Compound (1-1), Compound (1-NF-1), and Compound (1-N-1))

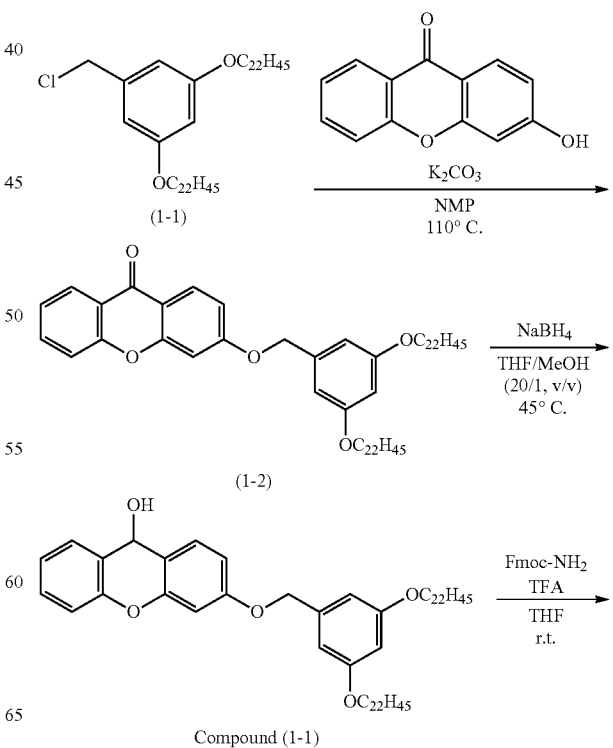

Compound (1-1)

-continued

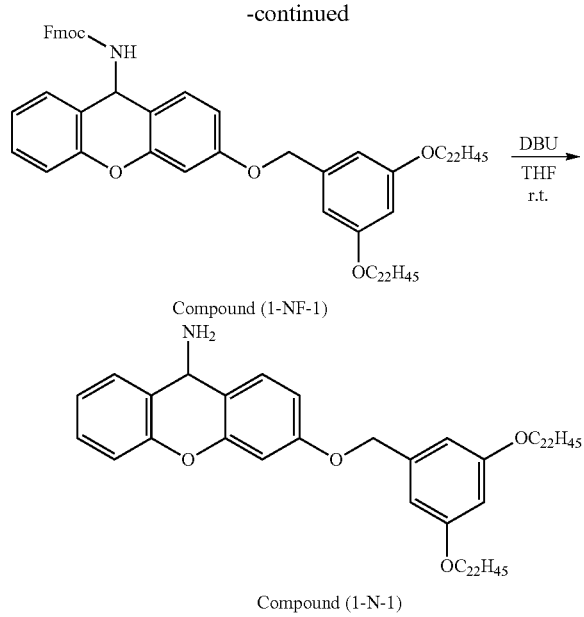

Compound (1-NF-1)

Compound (1-N-1)

An intermediate (1-1) was synthesized according to the method described in EP2518041A.

The intermediate (1-1) (4.00 g, 5.16 mmol), 3-hydroxyxanthen-9-one (1.31 g, 6.24 mmol), potassium carbonate (1.43 g, 10.3 mmol), and N-methylpyrrolidone (NMP, 40 mL) were mixed, and the mixture was stirred at 110° C. for 3 hours under a nitrogen atmosphere. The reaction solution was cooled to 55° C. and extracted with toluene and water. Methanol was added to the obtained organic layer to precipitate solid, and the solid was filtered and dried under reduced pressure to obtain an intermediate (1-2) (4.66 g, yield: 95%).

The intermediate (1-2) (4.66 g, 4.90 mmol), sodium borohydride (0.57 g, 14.7 mmol), and tetrahydrofuran (47 mL) were mixed under a nitrogen atmosphere, the mixture was stirred at 45° C., and then methanol (2.3 mL) was added dropwise thereto. The reaction solution was stirred at 45° C. for 3 hours, and methanol (93 mL) was gently added dropwise thereto. The obtained slurry was stirred at 45° C. for 30 minutes and cooled to room temperature in a water bath, and the precipitated solid was filtered and dried to obtain a compound (1-1) (4.58 g, yield: 98%).

$^1$H-NMR (CDCl$_3$, 300 MHz): δ=0.88 (6H, t), 1.19 to 1.50 (76H, m), 1.77 (4H, m), 1.92 (1H, d), 3.94 (4H, t), 5.02 (2H, s), 5.79 (1H, d), 6.41 (1H, t), 6.57 (2H, d), 6.74 (1H, d), 6.83 (1H, dd), 7.13 to 7.20 (2H, m), 7.35 (1H, td), 7.49 (1H, d), 7.59 (1H, d)

The compound (1-1) (4.58 g, 4.80 mmol), 9-fluorenylmethyl carbamate (Fmoc-NH$_2$, 2.30 g, 9.61 mmol), and tetrahydrofuran (46 mL) were mixed and completely dissolved at 40° C., the solution was cooled to room temperature, and trifluoroacetic acid (0.36 ml, 4.8 mmol) was added dropwise thereto. The reaction solution was stirred at room temperature for 1 hour, methanol (93 mL) was added thereto to precipitate solid, and the solid was filtered and dried to obtain crude crystals. The obtained crude crystals were purified by silica gel column chromatography (hexane:ethyl acetate=9:1 to 4:1) to obtain a compound (1-NF-1) (4.61 g, yield: 82%).

$^1$H-NMR (CDCl$_3$, 300 MHz): δ=0.88 (6H, t), 1.19 to 1.50 (76H, m), 1.77 (4H, m), 3.94 (4H, t), 4.23 (1H, t), 4.52 (2H, d), 5.00 (2H, s), 5.19 (1H, d), 6.13 (1H, d), 6.41 (1H, t), 6.56 (2H, d), 6.69 (1H, d), 6.77 (1H, dd), 7.11 (2H, t), 7.25 to 7.46 (7H, m), 7.58 (2H, d), 7.75 (2H, d)

The compound (1-NF-1) (1.51 g, 1.29 mmol) was mixed with tetrahydrofuran (20 mL), diazabicycloundecene (DBU, 391 μL, 2.57 mmol) was added thereto, and the mixture was stirred at room temperature for 2 hours. After the reaction was completed, acetonitrile (80 mL) was added thereto and stirred, and then the precipitate was filtered and dried under reduced pressure to obtain a compound (1-N-1) (1.15 g, yield: 94%).

$^1$H-NMR (CDCl$_3$, 300 MHz): δ=0.88 (6H, t), 1.20 to 1.50 (76H, m), 1.76 (4H, m), 3.94 (4H, t), 5.00 (2H, s), 5.03 (1H, s), 6.40 (1H, t), 6.57 (2H, d), 6.72 (1H, d), 6.78 (1H, dd), 7.09 to 7.15 (2H, m), 7.25 to 7.29 (1H, m), 7.38 (1H, d), 7.48 (1H, dd)

Synthesis of Protective Group-Forming Reagent (Compound (1-NF-2))

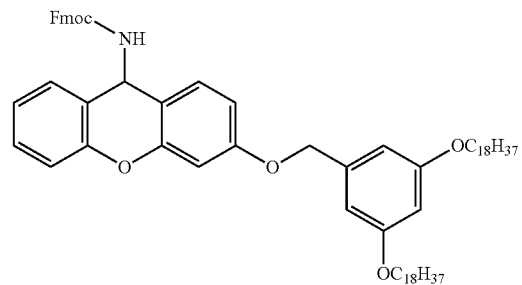

Compound (1-NF-2)

A compound (1-NF-2) was obtained by synthesizing in the same manner as in the compound (1-NF-1).

$^1$H-NMR (CDCl$_3$, 300 MHz): δ=0.88 (6H, t), 1.19 to 1.50 (60H, m), 1.77 (4H, m), 3.94 (4H, t), 4.23 (1H, t), 4.52 (2H, d), 5.00 (2H, s), 5.19 (1H, d), 6.13 (1H, d), 6.41 (1H, t), 6.56 (2H, d), 6.69 (1H, d), 6.77 (1H, dd), 7.11 (2H, t), 7.25 to 7.46 (7H, m), 7.58 (2H, d), 7.75 (2H, d)

Synthesis of Protective Group-Forming Reagent (Compound (1-NF-3))

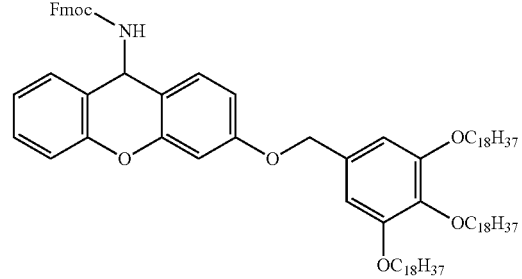

Compound (1-NF-3)

A compound (1-NF-3) was obtained by synthesizing in the same manner as in the compound (1-NF-1).

$^1$H-NMR (CDCl$_3$, 300 MHz): δ=0.88 (9H, t), 1.19 to 1.50 (90H, m), 1.70 to 1.85 (6H, m), 3.97 (6H, m), 4.23 (1H, t), 4.53 (2H, d), 4.96 (2H, s), 5.21 (1H, d), 6.14 (1H, d), 6.63

(2H, s), 6.71 (1H, d), 6.78 (1H, dd), 7.08 to 7.19 (2H, m), 7.25 to 7.47 (7H, m), 7.58 (2H, d), 7.75 (2H, d)

Synthesis of Comparative Protective Group-Forming Reagent (Comparative Compound (1-NF-1))

A comparative compound (1-NF-1) was synthesized according to the method described in paragraphs 0113 to 0118 of WO2018/021322A.

Comparative compound (1-NF-1)

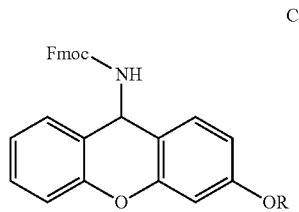

Synthesis of Comparative Protective Group-Forming Reagent (Comparative Compound (2-NF-1))

A comparative compound (2-NF-1) was synthesized according to the method described in paragraphs 0147 to 0152 of WO2010/113939A.

Comparative compound (2-NF-1)

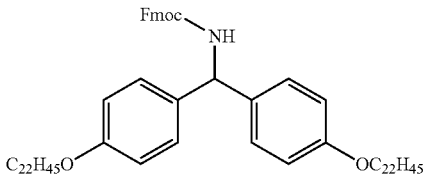

Example 1

Synthesis of Protected Amino Acid Compound (N-Terminal and C-Terminal Protected Amino Acid (2))

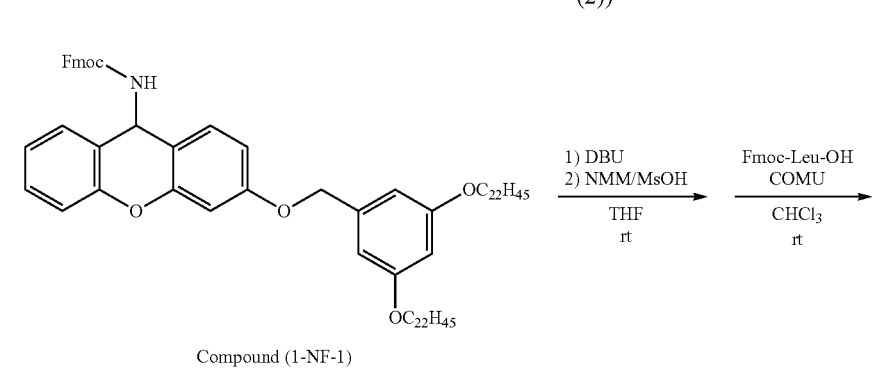

Compound (1-NF-1)

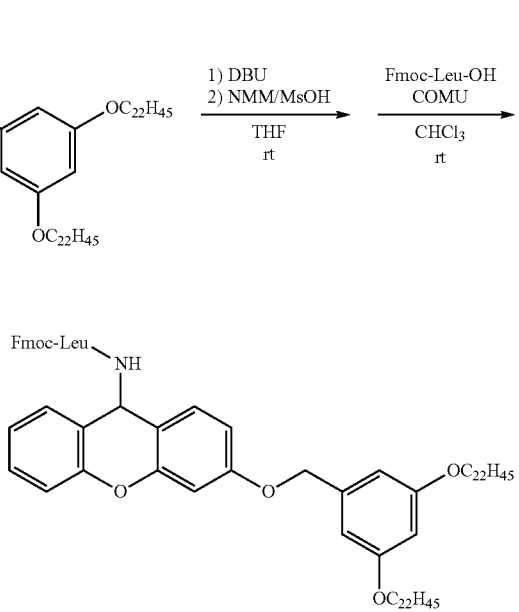

N-protected and C-protected amino acid (1-N-1)

-continued

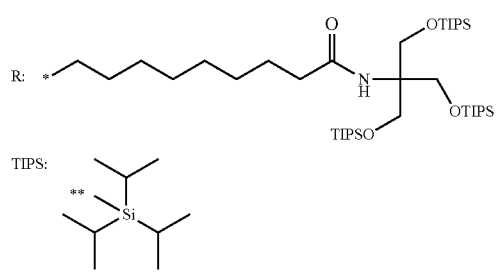

The compound (1-NF-1) (1.00 g, 0.851 mmol) was dissolved in tetrahydrofuran (8.5 mL), and diazabicycloundecene (DBU, 2.0 molar equivalent) was added thereto and stirred. After the deprotection reaction was completed, N-methylmorpholine (NMM, 2.05 molar equivalent) and methanesulfonic acid (MsOH, 2.0 molar equivalent) were added thereto in sequence, and N-[(9H-fluoren-9-yl-methoxy)carbonyl]-L-leucine (Fmoc-Leu-OH, 1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (43 mL) was added thereto and stirred, and then the precipitate was filtered, washed with acetonitrile, and dried under reduced pressure to obtain an N-protected and C-protected amino acid (1-N-1) (1.08 g, yield: 98.4%). Fmoc represents an Fmoc group, and Leu represents a leucine residue.

Examples 2 and 3 and Comparative Examples 1 and 2

Same as the method for obtaining the N-protected and C-protected amino acid (1-N-1), the corresponding N-protected and C-protected amino acid was synthesized by condensing the compound (1-NF-2), compound (1-NF-3), comparative compound (1-NF-1), or comparative compound (2-NF-1) with N-[(9H-fluoren-9-ylmethoxy)carbonyl]-L-leucine.

(Evaluation 1)

<Deprotection Rate>

With regard to the N-terminal and C-terminal protected amino acid compounds synthesized above, the deprotection ratio (deprotection ratio of C-terminal end) of the protected carboxamide moiety was determined as follows.

100 mg of Fmoc-Leu-NH-Tag (N-terminal and C-terminal protected amino acids of the compounds of Examples and N-terminal and C-terminal protected amino acids of the compounds of Comparative Examples) and Fmoc-Gly-OH (internal standard) in an equimolar amount of Fmoc-Leu-NH-Tag were mixed, and then chloroform/triisopropylsilane/3,6-dioxa-1,8-octanedithiol/water/trifluoroacetic acid (87.5/2.5/2.5/2.5/5: vol %) was added thereto so that the substrate concentration was 0.025 M based on Fmoc-Leu-NH-Tag, and the mixture was stirred at 30° C. for 60 minutes.

5 µL of the reaction solution was dissolved in 400 µL of methanol (MeOH), and using Ultra Performance LC (ultra-performance liquid chromatography, manufactured by Waters Corporation, model number: ACQUITY), the deprotection ratio (%) was determined by quantifying the ratio of Fmoc-Leu-NH$_2$ and Fmoc-Gly-OH produced by deprotecting Fmoc-Leu-NH-Tag, and evaluated based on the following standard.

The columns and measurement conditions used for the ultra-performance liquid chromatography are shown below.

Column: manufactured by Waters Corporation, model number: BEH C18 1.7 µm, 2.1 mm×30 mm Flow rate: 0.5 mL/min Solvent: solution A: 0.1% formic acid-water, solution B: 0.1% formic acid-acetonitrile Gradient cycle: 0.00 min (solution A/solution B=95/5), 2.00 min (solution A/solution B=5/95), 3.00 min (solution A/solution B=95/5)

Detection wavelength: 254 nm

Regarding the evaluation of the deprotection rate, a case of "B" or higher was regarded as acceptable. The results are shown in Table 1.

It can be said that, as the deprotection ratio is higher, the deprotection rate is higher and the deprotection rate is excellent.

—Evaluation Standard—

"A": deprotection ratio was 90% or more.

"B": deprotection ratio was 50% or more and less than 90%.

"C": deprotection ratio was 10% or more and less than 50%.

"D": deprotection ratio was less than 10%.

<Temporal Stability>

After storing the N-protected and C-protected amino acid (10 mg) obtained above in a constant-temperature tank at 50° C. in the air for 3 days, the amount of remaining N-protected and C-protected amino acid was determined and evaluated based on the following standard. The results are shown in Table 1.

Regarding the evaluation of the temporal stability, a case of "B" or higher was regarded as acceptable.

It can be said that, as survival rate of the N-protected and C-protected amino acid is higher, temporal stability of the peptide compound is high, side reactions can be suppressed, and yield is excellent.

—Evaluation Standard—

"A": survival rate was 98% or more.

"B": survival rate was 96% or more and less than 98%.

"C": survival rate was 94% or more and less than 96%.

"D": survival rate was less than 94%.

TABLE 1

| | | Evaluation | |
|---|---|---|---|
| | Type of compound | Deprotection rate | Temporal stability |
| Example 1 | Compound 1-NF-1 | A | A |
| Example 2 | Compound 1-NF-2 | A | A |
| Example 3 | Compound 1-NF-3 | A | A |
| Comparative example 1 | Comparative compound 1-NF-1 | A | C |
| Comparative example 2 | Comparative compound 1-NF-2 | D | A |

From Table 1, the compound represented by Formula (1) used in Examples 1 to 3 is superior in both deprotection rate and temporal stability as compared with the compound of Comparative Examples 1 and 2.

Synthesis of Protected Peptide (5-Residue Peptide: Fmoc-MeNle-MeNle-Arg(Pbf)-Cys(Trt)-Gly-NH-Protective Group)

Details of each abbreviation other than the above are shown below.

MeNle: N-methylnorleucine residue

Arg(Pbf): Pbf-protected arginine residue

Pbf: 2,2,4,6,7-pentamethyldihydrobenzofuran-5-sulfonyl group

Cys(Trt): Trt-protected cysteine residue

Trt: triphenylmethyl group

Gly: glycine residue (Example 4: Synthesis of Fmoc-Gly-NH-XantTAG (1))

9H-fluoren-9-ylmethyl N-(3-(3,5-bis (docosyloxy)benzyloxy)-9H-xanthen-9-yl) carbamate (corresponding to the above-described compound (1-1); also referred to as "Fmoc-NH-XantTAG (1)") (2.00 g, 1.70 mmol) was dissolved in tetrahydrofuran (17 mL), and diazabicycloundecene (DBU, 2.0 molar equivalent) were added thereto and stirred. After the deprotection reaction was completed, N-methylmorpholine (2.05 molar equivalent) and methanesulfonic acid (2.0 molar equivalent) were added thereto in sequence, and Fmoc-Gly-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (85 mL) was added thereto and stirred, and then the precipitate was filtered, washed with acetonitrile, and dried under reduced pressure to obtain Fmoc-Gly-NH-XantTAG (1) (2.09 g, yield: 99.7%).

(Example 5: Synthesis of
Fmoc-Cys(Trt)-Gly-NH-XantTAG (1))

Fmoc-Gly-NH-XantTAG (1) (2.09 g, 1.70 mmol) was dissolved in tetrahydrofuran (17 mL), and diazabicycloundecene (DBU, 2.0 molar equivalent) was added thereto and stirred. After the deprotection reaction was completed, N-methylmorpholine (2.05 molar equivalent) and methanesulfonic acid (2.0 molar equivalent) were added thereto in sequence, and Fmoc-Cys(Trt)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (85 mL) was added thereto and stirred, and then the precipitate was filtered, washed with acetonitrile, and dried under reduced pressure to obtain Fmoc-Cys(Trt)-Gly-NH-XantTAG (1) (2.64 g, yield: 98.6%).

(Example 6: Synthesis of Fmoc-Arg(Pbf)-Cys(Trt)-Gly-NH-XantTAG (1))

Fmoc-Cys(Trt)-Gly-NH-XantTAG (1) (2.50 g, 1.58 mmol) was dissolved in tetrahydrofuran (16 mL), and diazabicycloundecene (DBU, 2.0 molar equivalent) was added thereto and stirred. After the deprotection reaction was completed, N-methylmorpholine (2.05 molar equivalent) and methanesulfonic acid (2.0 molar equivalent) were added thereto in sequence, and Fmoc-Arg(Pbf)-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (79 mL) was added thereto and stirred, and then the precipitate was filtered, washed with acetonitrile, and dried under reduced pressure to obtain Fmoc-Arg(Pbf)-Cys(Trt)-Gly-NH-XantTAG (1) (3.04 g, yield: 96.6%).
ESI-MS(+)=1985.1

(Example 7: Synthesis of Fmoc-MeNle-Arg(Pbf)-Cys(Trt)-Gly-NH-XantTAG (1))

Fmoc-Arg(Pbf)-Cys(Trt)-Gly-NH-XantTAG (1) (2.50 g, 1.26 mmol) was dissolved in tetrahydrofuran (13 mL), and diazabicycloundecene (DBU, 2.0 molar equivalent) was added thereto and stirred. After the deprotection reaction was completed, N-methylmorpholine (2.05 molar equivalent) and methanesulfonic acid (2.0 molar equivalent) were added thereto in sequence, and Fmoc-MeNle-OH (1.25 molar equivalent) and (1-cyano-2-ethoxy-2-oxoethylidenaminooxy)dimethylamino-morpholino-carbenium hexafluorophosphate (COMU, 1.25 molar equivalent) were added thereto and stirred. After the condensation reaction was completed, acetonitrile (63 mL) was added thereto and stirred, and then the precipitate was filtered, washed with acetonitrile, and dried under reduced pressure to obtain Fmoc-MeNle-Arg(Pbf)-Cys(Trt)-Gly-NH-XantTAG (1) (2.53 g, yield: 95.1%).

(Example 8: Synthesis of Fmoc-MeNle-MeNle-Arg(Pbf)-Cys(Trt)-Gly-NH-XantTAG (1))

Fmoc-MeNle-Arg(Pbf)-Cys(Trt)-Gly-NH-XantTAG (1) (2.00 g, 1.70 mmol) was dissolved in tetrahydrofuran (17 mL), and diazabicycloundecene (DBU, 2.0 molar equivalent) was added thereto and stirred. After the deprotection reaction was completed, N,N-diisopropylethylamine (6.05 molar equivalent) and methanesulfonic acid (2.0 molar equivalent) were added thereto in sequence, and Fmoc-MeNle-OH (2.0 molar equivalent) and (7-azabenzotriazole-1-yloxy)tripyrolidinophosphonium hexafluorophosphate (PyAOP, 2.0 molar equivalent) were added thereto and stirred. After the condensation reaction was completed, acetonitrile (57 mL) was added thereto and stirred, and then the precipitate was filtered, washed with acetonitrile, and dried under reduced pressure to obtain Fmoc-MeNle-MeNle-Arg(Pbf)-Cys(Trt)-Gly-NH-XantTAG (1) (2.43 g, yield: 94.7%).

As shown in Examples 4 to 8, in all examples of the method for producing a peptide compound, which includes a step of using the compound represented by Formula (1) according to the present disclosure, it can be seen that the yield of the obtained peptide compound is high and the total yield is also excellent.

<15-Residue Peptide: Synthesis of ClAc-Phe-MeAla-Asn(Trt)-Pro-His(Boc)-Leu-Ser(Trt)-Trp(Boc)-Ser(Trt)-Trp(Boc)-MeNle-M eNle-Arg(Pbf)-Cys(Trt)-Gly-NH-Protective Group>

Details of each abbreviation other than the above are shown below.
Trp(Boc): Boc-protected tryptophan residue
Boc: tert-butoxycarbonyl group
Ser(Trt): Trt-protected serine residue
Leu: leucine residue
His(Boc): Boc-protected histidine residue
Asn(Trt): Trt-protected asparagine residue
MeAla: N-methylalanine residue
Phe: phenylalanine residue
ClAc: chloroacetyl group Synthesis of ClAc-Phe-MeAla-Asn(Trt)-Pro-His(Boc)-Leu-Ser(Trt)-Trp(Boc)-Ser(Trt)-Trp(Boc)-MeNle-M eNle-Arg(Pbf)-Cys(Trt)-Gly-NH-XantTAG (1)

Using the Fmoc-MeNle-MeNle-Arg(Pbf)-Cys(Trt)-Gly-NH-XantTAG (1) obtained in Example 8, a peptide chain was extended by repeating the removal of the Fmoc group and the condensation reaction of the amino acid or carboxylic acid shown in Table 2 below. THF was used as the reaction solvent, and acetonitrile was used as the polar solvent in the precipitating step. The proportion of THF and acetonitrile used in the precipitating step was 1:5 or 1:10.

TABLE 2

| Step | Amino acid or carboxylic acid to be condensed | Synthesis method | Yield (%) |
|---|---|---|---|
| 1st residue | Fmoc-Trp(Boc)-OH | Same as Example 8 | 99.6 |
| 2nd residue | Fmoc-Ser(Trt)-OH | Same as Example 7 | 94.8 |
| 3rd residue | Fmoc-Trp(Boc)-OH | Same as Example 7 | 98.8 |
| 4th residue | Fmoc-Ser(Trt)-OH | Same as Example 7 | 97.2 |
| 5th residue | Fmoc-Leu-OH | Same as Example 7 | 99.2 |
| 6th residue | Fmoc-His(Boc)-OH | Same as Example 7 | 97.9 |
| 7th residue | Fmoc-Pro-OH | Same as Example 7 | 97.2 |
| 8th residue | Fmoc-Asn(Trt)-OH | Same as Example 7 | 96.7 |
| 9th residue | Fmoc-MeAla-OH | Same as Example 7 | 94.9 |
| 10th residue | Fmoc-Phe-OH | Same as Example 8 | 96.7 |
| 11th residue | Chloroacetic acid | Same as Example 7 | 97.5 |

<Peptide Deprotection and Cyclization Step>

Synthesis of ClAc-Phe-MeAla-Asn-Pro-His-Leu-Ser-Trp-Ser-Trp-MeNle-MeNle-Arg-Cys-Gy-NH₂

Under room temperature, a 92.5/2.5/2.5/2.5 mixed solution (6.9 mL) of trifluoroacetic acid, triisopropylsilane, 3,6-dioxa-1,8-octanedithiol, and water was added to ClAc-Phe-MeAla-Asn(Trt)-Pro-His(Boc)-Leu-Ser(Trt)-Trp(Boc)-Ser(Trt)-Trp(Boc)-MeNle-M eNle-Arg(Pbf)-Cys(Trt)-Gly-NH-XantTAG (1) (0.300 g, 0.0665 mmol), and the mixture was stirred for 30 minutes. A 1/1 mixed solution (69 mL) of tert-butyl methyl ether and n-hexane was added to the reaction solution and stirred, and the mixture was centrifugated to remove a supernatant solution. After repeating the addition of tert-butyl methyl ether (69 mL) to the precipitate, stirring, centrifugation, and removal of the supernatant solution twice, the resultant was dried under reduced pressure to obtain ClAc-Phe-MeAla-Asn-Pro-His-Leu-Ser-Trp-Ser-Trp-MeNle-MeNle-Arg-Cys-Gy-NH$_2$ (0.167 g).

Example 9: Synthesis of Cyclic Peptide A

Under room temperature, a 1/1 mixed solution (138 mL) of acetonitrile and a 0.1 mol/L of triethylammonium dicarbonate buffer solution and a 0.5 mol/L of tris(2-carboxyethyl)phosphine aqueous solution (138 µL) were added to ClAc-Phe-MeAla-Asn-Pro-His-Leu-Ser-Trp-Ser-Trp-MeNle-MeNle-Arg-Cys-Gy-NH$_2$ (0.167 g), and the mixture was stirred for 2 hours. After the cyclization reaction was completed, the resultant was concentrated under reduced pressure to obtain a cyclic peptide A (0.145 g) having the following structure.

HPLC purity (220 nm): 89.6%
MS (ESI, m/Z): 1868.3 (M+H), 1866.3 (M−H)

Cyclic peptide A

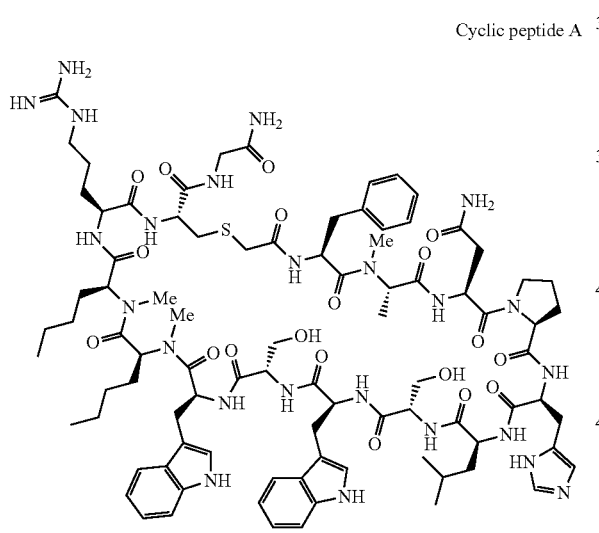

<15-Residue Peptide: Synthesis of ClAc-Phe-MeAla-Asn(Mmt)-Pro-His(Mmt)-Leu-Ser(Trt)-Trp-Ser(Trt)-Trp-MeNle-MeNle-Ar g(Pbf)-Cys(Mmt)-Gly-NH-Protective Group>

Details of each abbreviation other than the above are shown below.
Cys(Mmt): Mmt-protected cysteine residue
Mmt: 4-methoxytrityl group
His(Mmt): Mmt-protected histidine residue
Asn(Mmt): Mmt-protected asparagine residue Synthesis of ClAc-Phe-MeAla-Asn(Mmt)-Pro-His (Mmt)-Leu-Ser(Trt)-Trp-Ser(Trt)-Trp-MeNle-MeNle-Ar g(Pbf)-Cys(Mmt)-Gly-NH-XantTAG (1)

Using the Fmoc-Gly-NH-XantTAG (1) obtained in Example 4, a peptide chain was extended by repeating the removal of the Fmoc group and the condensation reaction of the amino acid or carboxylic acid shown in Table 3 below.

TABLE 3

| Step | Amino acid or carboxylic acid to be condensed | Synthesis method | Yield (%) |
|---|---|---|---|
| 1st residue | Fmoc-Cys(Mmt)-OH | Same as Example 7 | 97.4 |
| 2nd residue | Fmoc-Arg(Pbf)-OH | Same as Example 7 | 100 |
| 3rd residue | Fmoc-MeNle-OH | Same as Example 7 | 94.4 |
| 4th residue | Fmoc-MeNle-OH | Same as Example 8 | 97.8 |
| 5th residue | Fmoc-Trp-OH | Same as Example 8 | 99.8 |
| 6th residue | Fmoc-Ser(Trt)-OH | Same as Example 7 | 94.1 |
| 7th residue | Fmoc-Trp-OH | Same as Example 7 | 100 |
| 8th residue | Fmoc-Ser(Trt)-OH | Same as Example 7 | 98.1 |
| 9th residue | Fmoc-Leu-OH | Same as Example 7 | 100 |
| 10th residue | Fmoc-His(Mmt)-OH | Same as Example 7 | 95.5 |
| 11th residue | Fmoc-Pro-OH | Same as Example 7 | 93.3 |
| 12th residue | Fmoc-Asn(Mmt)-OH | Same as Example 7 | 98.9 |
| 13th residue | Fmoc-MeAla-OH | Same as Example 7 | 85.8 |
| 14th residue | Fmoc-Phe-OH | Same as Example 8 | 99.8 |
| 15th residue | Chloroacetic acid | Same as Example 7 | 89.7 |

<Peptide Deprotection and Cyclization Step>

Synthesis of ClAc-Phe-MeAla-Asn(Mmt)-Pro-His-Leu-Ser-Trp-Ser-Trp-MeNle-MeNle-Arg(Pbf)-Cys-Gly NH$_2$ Under room temperature, trifluoroacetic acid/hexafluoroisopropanol/dichloromethane (1/10/100: vol %, 1.14 mL), triisopropylsilane (10.0 molar equivalent), and 3,6-dioxa-1,8-octanedithiol (10.0 molar equivalent) were added to ClAc-Phe-MeAla-Asn(Mmt)-Pro-His(Mmt)-Leu-Ser(Trt)-Trp-Ser(Trt)-Trp-MeNle-MeNle-Ar g(Pbf)-Cys(Mmt)-Gly-NH-XantTAG (1) (50 mg, 0.0114 mmol), and the mixture was stirred for 1 hour. A 1/1 mixed solution (10 mL) of tert-butyl methyl ether and n-hexane was added to the reaction solution and stirred, and the mixture was centrifugated to remove a supernatant solution. After repeating the addition of tert-butyl methyl ether (69 mL) to the precipitate, stirring, centrifugation, and removal of the supernatant solution twice, the resultant was dried under reduced pressure to obtain ClAc-Phe-MeAla-Asn(Mmt)-Pro-His-Leu-Ser-Trp-Ser-Trp-MeNle-MeNle-Arg(Pbf)-Cys-Gly-NH$_2$ (40.4 mg).

Example 10: Synthesis of Cyclic Peptide B

Under room temperature, a 1/1 mixed solution (11 mL) of acetonitrile and a 0.1 mol/L of triethylammonium dicarbonate buffer solution and a 0.5 mol/L of tris(2-carboxyethyl) phosphine aqueous solution (23 µL) were added to ClAc-Phe-MeAla-Asn(Mmt)-Pro-His-Leu-Ser-Trp-Ser-Trp-MeNle-MeNle-Arg(Pbf)-Cys-Gly-NH$_2$ (39.4 mg), and the mixture was stirred for 2 hours. After the cyclization reaction was completed, the resultant was concentrated under reduced pressure to obtain a cyclic peptide B (32.7 mg) having the following structure.

HPLC purity (220 nm): 88.5%
MS (ESI, m/Z): 1197.6 (M+H)/2, 1195.6 (M−H)/2

Cyclic peptide B

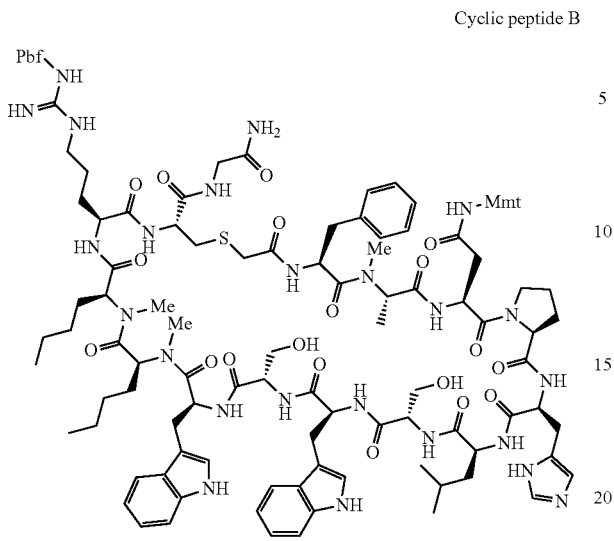

As shown in Examples 9 and 10, the method for producing a peptide compound according to the embodiment of the present disclosure can also be applied to a production of a cyclic peptide compound having an N-alkylamide structure. The C-terminal protective group can be deprotected even under weak acid conditions, a side reaction of the obtained peptide can be suppressed, the purity is high, and the yield is high.

The disclosure of Japanese Patent Application No. 2019-122492 filed on Jun. 28, 2019 and the disclosure of Japanese Patent Application No. 2019-221545 filed on Dec. 6, 2019 are incorporated in the present specification by reference.

All documents, patent applications, and technical standards described in the present specification are incorporated herein by reference to the same extent as in a case of being specifically and individually noted that individual documents, patent applications, and technical standards are incorporated by reference.

What is claimed is:

1. A method for producing a peptide compound, comprising:
a step of using a compound represented by Formula (1),

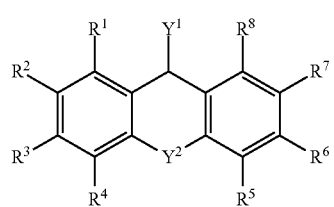

(1)

in Formula (1), $Y^1$ represents —SH, Br, Cl, —OH, —NH$_2$, —NHEt, where Et represents an ethyl group, or —NHFmoc, where Fmoc represents a 9-fluorenylmethoxycarbonyl group, $Y^2$ represents —O—, —S—, —CH=CH—, —C(CH$_3$)=C(CH$_3$)—, —CH$_2$—CH$_2$—, —C(CH$_3$)$_2$—,

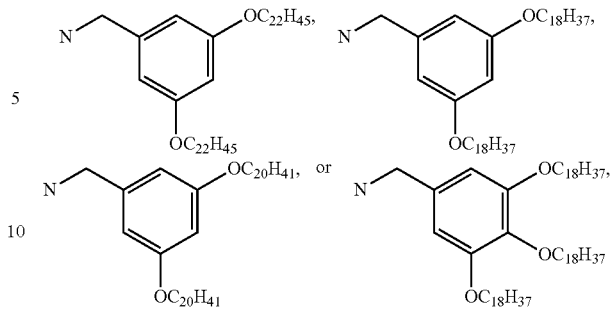

$R^1$, $R^2$, $R^5$, $R^7$, and $R^8$ each represent a hydrogen atom, $R^3$ represents a hydrogen atom,

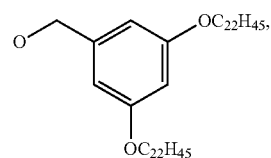

—OC$_{22}$H$_{45}$, or —OC$_{12}$H$_{24}$OC$_{22}$H$_{45}$,
$R^4$ represents a hydrogen atom or —NH$_2$,
$R^6$ represents a hydrogen atom,

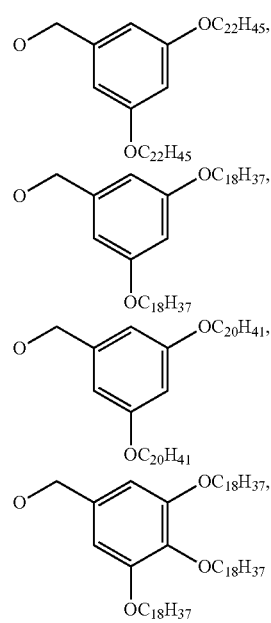

—OC$_{22}$H$_{45}$, or —OC$_{12}$H$_{24}$OC$_{22}$H$_{45}$,
provided that at least one of the following (i), (ii), or (iii) is satisfied:
(i) $Y^2$ represents

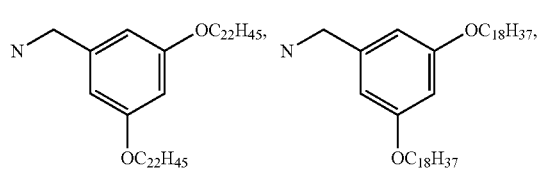

-continued

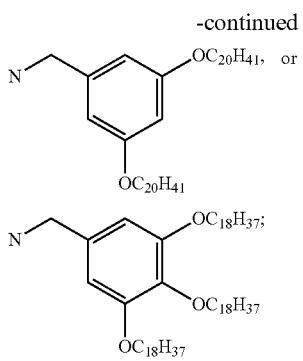

(ii) $R^3$ represents

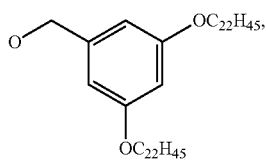

—$OC_{22}H_{45}$, or —$OC_{12}H_{24}OC_{22}H_{45}$; or (iii) $R^6$ represents

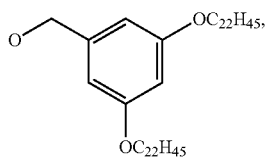

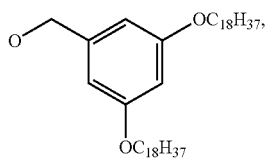

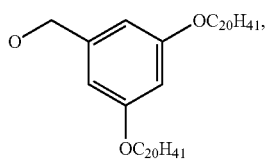

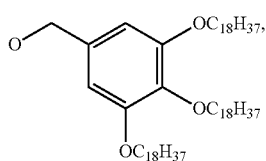

—$OC_{22}H_{45}$, or —$OC_{12}H_{24}OC_{22}H_{45}$.

2. The method for producing a peptide compound according to claim 1,
wherein the step of using the compound represented by Formula (1) is a C-terminal protecting step of protecting a carboxy group or an amide group of an amino acid compound or a peptide compound with the compound represented by Formula (1).

3. The method for producing a peptide compound according to claim 2,
wherein the amino acid compound or the peptide compound in the C-terminal protecting step is an N-terminal protected amino acid compound or an N-terminal protected peptide compound, and
the method for producing a peptide compound further comprising:
an N-terminal deprotecting step of deprotecting an N-terminal end of an N-terminal and C-terminal protected amino acid compound or an N-terminal and C-terminal protected peptide compound, which is obtained in the C-terminal protecting step,
a peptide chain extending step of condensing the N-terminal end of a C-terminal protected amino acid compound or a C-terminal protected peptide compound, which is obtained in the N-terminal deprotecting step, with an N-terminal protected amino acid compound or an N-terminal protected peptide compound; and
a precipitating step of precipitating the N-terminal and C-terminal protected peptide compound obtained in the peptide chain extending step.

4. The method for producing a peptide compound according to claim 3, further comprising, one or more times in the following order after the precipitating step:
a step of deprotecting the N-terminal end of the obtained N-terminal and C-terminal protected peptide compound;
a step of condensing the N-terminal end of the obtained C-terminal protected peptide compound with an N-terminal protected amino acid compound or an N-terminal protected peptide compound; and
a step of precipitating the obtained N-terminal and C-terminal protected peptide compound.

5. The method for producing a peptide compound according to claim 1, further comprising:
a C-terminal deprotecting step of deprotecting a C-terminal protective group using an acid catalyst,
wherein the acid catalyst is trifluoroacetic acid, and
the concentration of trifluoroacetic acid is 10% by mass or less.

6. The method for producing a peptide compound according to claim 1,
wherein only one of (ii) or (iii) is satisfied.

7. The method for producing peptide according to claim 1,
wherein at least one of (ii) or (iii) is satisfied.

* * * * *